US008835616B2

(12) United States Patent
Moll et al.

(10) Patent No.: US 8,835,616 B2
(45) Date of Patent: Sep. 16, 2014

(54) METHODS FOR THE PRODUCTION AND SECRETION OF MODIFIED PEPTIDES

(75) Inventors: Gert Nikolaas Moll, Groningen (NL); Anneke Kuipers, Haule (NL); Rick Rink, Groningen (NL); Arnold Jacob Mathieu Driessen, Groningen (NL); Oscar Paul Kuipers, Groningen (NL)

(73) Assignee: Lanthiopep B.V., Groningen (NL)

( * ) Notice: Subject to any disclaimer, the term of this patent is extended or adjusted under 35 U.S.C. 154(b) by 1324 days.

(21) Appl. No.: 11/792,516

(22) PCT Filed: Dec. 7, 2005

(86) PCT No.: PCT/NL2005/000842
§ 371 (c)(1),
(2), (4) Date: Aug. 6, 2007

(87) PCT Pub. No.: WO2006/062398
PCT Pub. Date: Jun. 15, 2006

(65) Prior Publication Data
US 2009/0042246 A1    Feb. 12, 2009

(30) Foreign Application Priority Data

Dec. 7, 2004  (EP) ..................... 04078318

(51) Int. Cl.
*C07H 21/04* (2006.01)
*C12P 21/06* (2006.01)
*C12N 15/62* (2006.01)

(52) U.S. Cl.
CPC .................. *C12N 15/625* (2013.01)
USPC ........................ 536/23.4; 435/69.1

(58) Field of Classification Search
None
See application file for complete search history.

(56) References Cited

U.S. PATENT DOCUMENTS 5,939,317 A * 8/1999 Fayard et al. ............. 435/320.1
6,541,607 B1 * 4/2003 Hansen ..................... 530/350
(Continued)

FOREIGN PATENT DOCUMENTS

EP       0 543 195 A2     5/1993
EP       040783318.5   * 12/2004 ............. C12N 15/00
(Continued)

OTHER PUBLICATIONS

Kuipers et al., NisT. The Transporter of the Lantibiotic Nisin, Can Transport Fully Modified, Dehydrated, and Unmodified Prenisin and Fusions of the Leasder Peptide with Non-lantibiotic Peptides., The Journal of Biological Chemistry; May 21, 2004, vol. 279, pp. 21176-21182.*

(Continued)

*Primary Examiner* — Alexander Kim
(74) *Attorney, Agent, or Firm* — TraskBritt, P.C.

(57) ABSTRACT

The invention relates to the production of heterologous polypeptides in a recombinant host cell. More specifically, it relates to the production and secretion of peptides, such as biologically active peptides, that are modified by one or more lantibiotic-synthesizing enzymes. Provided is a nucleic acid construct encoding a polypeptide comprising 1) a non-lantibiotic export signal that is recognized by a non-lantibiotic export system; 2) a lantibiotic leader peptide that is recognized by at least a lantibiotic dehydratase such as LanB and, C-terminally of said export signal and said leader peptide, 3) a peptide of interest containing one or more serine or threonine residue(s) which can be posttranslationally dehydrated by said dehydratase. Also provided is a method for producing a polypeptide in a host cell, comprising providing a host cell with a nucleic acid construct according to the invention and allowing expression and secretion of the encoded polypeptide by said host cell, wherein said host cell comprises at least a dehydratase capable of modifying said encoded polypeptide and a non-lantibiotic export system capable of secreting said modified polypeptide.

22 Claims, 9 Drawing Sheets

(56) References Cited

U.S. PATENT DOCUMENTS

Figure 1A:
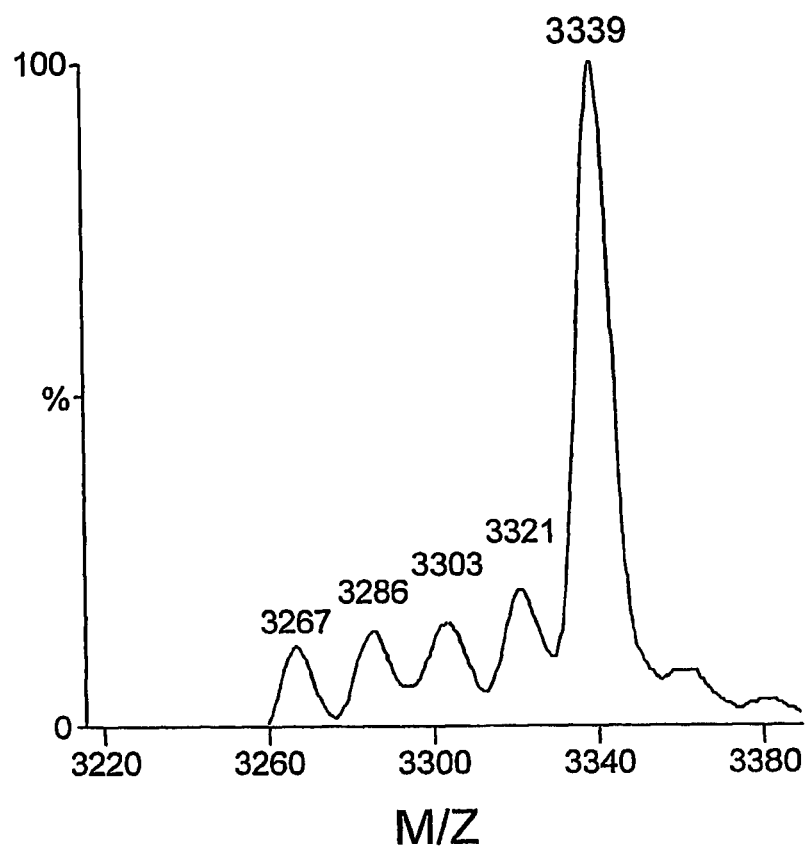

| | | | |
|---|---|---|---|
| 6,861,236 B2* | 3/2005 | Moll et al. | 435/69.1 |
| 2004/0009550 A1* | 1/2004 | Moll et al. | 435/69.1 |

FOREIGN PATENT DOCUMENTS

| | | |
|---|---|---|
| WO | WO 90/00558 | 1/1990 |
| WO | WO 03/099862 A1 | 12/2003 |
| WO | WO2006/062398 A2 | 6/2006 |

OTHER PUBLICATIONS

Twomey et al., Lantibiotics produced by lactic acid bacteria: structure, function and applications., Antonie van Leeuwenhoek, 2002, vol. 22, pp. 165-185.*

XP 002545660 (last viewed on Mar. 2, 2013).*

GenBank: EGD74539.1 (last viewed on Mar. 4, 2013).*

Tjalsma et al., Signal Pepetide-Dependent Protein Transport in *Bacillus subtilis*: a Genome-Based Survey of the Secretome., Microbiology and Molecular Biology Review (2000), vol. 64, pp. 515-547.*

Buchanan et al., A genetic screen for suppressors of *Escherichia coli* Tat signal peptide mutations establishes a critical role for the second arginine within the twin-arginine motif., Arch Microbiol (2001), vol. 177, pp. 107-112.*

Choi et al., Secetory and extracellular production of recombinant proteins using *Escherichia coli*., Appl Microbiol Biotechnol (2004), vol. 64, pp. 625-635.*

Widdick et al., Cloning and engineering of the cinnamycin biosynthetic gene cluster from *Streptomyces cinnamoneus* cinnamoneus DSM 40005., PNAS (Apr. 1, 2003), vol. 100, pp. 4316-4321.*

Rodriguez et al., Heterologous production of bacteriocins by lactic acid bacteria, International Journal of Food Microbiology, Jan. 25, 2003, pp. 101-116, vol. 80, No. 2.

Xie et al., Post-translational modifications during lactibiotic biosynthesis, Current Opinion in Chemical Biology, Oct. 2004, pp. 498-507, vol. 8, No. 5.

U.S. Appl. No. 12/387,373, filed May 1, 2009 Leenhouts et al. Immunization with Bacterial Ghost-Based Vaccines.

PCT International Search Report, PCT/NL2005/00842, dated Jun. 27, 2006.

Rodriguez et al., Abstract, Heterologous production of bacteriocins by lactic acid bacteria, International Journal of Food Microbiology, Jan. 25, 2003, pp. 101-116, vol. 80, No. 2.

Xie et al., Abstract, Post-translational modifications during lactibiotic biosynthesis, Current Opinion in Chemical Biology, Oct. 2004, pp. 498-507, vol. 8, No. 5.

Beck-Sickinger et al., Synthesis and conformational analysis of lantibiotic leader-, pro- and pre-peptides. Nisin and Novel Lantibiotics, 1991, pp. 218-229.

Chatterjee, et al., Biosynthesis and Mode of Action of Lantibiotics, Chem. Rev. 2005, pp. 633-683. vol. 105.

Sahl et al., Lantibiotics: Biosynthesis and Biological Activities of Uniquely Modified Peptides from Gram-Positive Bacteria, Annu. Rev. Microbiol., 1988, pp. 41-79, vol. 52.

Oman et al., Sublancin is Not a Lantibiotic but an S-linked Glycopeptide, Nature Chemical Biology, Feb. 2011, pp. 78-80, vol. 7.

Siegers et al. Biosynthesis of Lantibiotic Nisin, J. Biol. Chem. (1996) 271(21):12294-301.

Kiesau et al., Evidence for a Multimeric Subtilin Synthetase Complex, (1997) J. Bacteriol. 179(5):1475-1481.

* cited by examiner

SEQUENCE LISTING

<160> NUMBER OF SEQ ID NOS: 65

<210> SEQ ID NO 1
<211> LENGTH: 21
<212> TYPE: PRT
<213> ORGANISM: Streptomyces coelicolor strains

<400> SEQUENCE: 1

Met Asn Leu Phe Asp Leu Gln Ser Met Glu Thr Pro Lys Glu Ala
1               5                   10                  15

Met Gly Asp Val Glu
            20

<210> SEQ ID NO 2
<211> LENGTH: 26
<212> TYPE: PRT
<213> ORGANISM: Staphylococcus epidermidis BN280

<400> SEQUENCE: 2

Met Glu Asn Lys Lys Asp Leu Phe Asp Leu Glu Ile Lys Lys Asp Asn
1               5                   10                  15

Met Glu Asn Asn Asn Glu Leu Glu Ala Gln
            20                  25

<210> SEQ ID NO 3
<211> LENGTH: 26
<212> TYPE: PRT
<213> ORGANISM: Staphylococcus epidermidis strain 5

<400> SEQUENCE: 3

Met Lys Asn Asn Lys Asn Leu Phe Asp Leu Glu Ile Lys Lys Glu Thr
1               5                   10                  15

Ser Gln Asn Thr Asp Glu Leu Glu Pro Gln

<210> SEQ ID NO 4
<211> LENGTH: 24
<212> TYPE: PRT
<213> ORGANISM: Staphylococcus epidermidis K7

<400> SEQUENCE: 4

Met Asn Asn Ser Leu Phe Asp Leu Asn Leu Asn Lys Gly Val Glu Thr
1               5                   10                  15

Gln Lys Ser Asp Leu Ser Pro Gln
            20

<210> SEQ ID NO 5
<211> LENGTH: 23
<212> TYPE: PRT
<213> ORGANISM: Lactococcus lactis strains

<400> SEQUENCE: 5

Met Ser Thr Lys Asp Phe Asn Leu Asp Leu Val Ser Val Ser Lys Lys
1               5                   10                  15

Asp Ser Gly Ala Ser Pro Arg
            20

<210> SEQ ID NO 6
<211> LENGTH: 23
<212> TYPE: PRT
<213> ORGANISM: Lactococcus lactis 61-14

<400> SEQUENCE: 6

Met Ser Thr Lys Asp Phe Asn Leu Asp Leu Val Ser Val Ser Lys Thr
1               5                   10                  15

Asp Ser Gly Ala Ser Thr Arg
            20

<210> SEQ ID NO 7
<211> LENGTH: 24
<212> TYPE: PRT
<213> ORGANISM: Bacillus subtilis strains

<400> SEQUENCE: 7

Met Ser Lys Phe Asp Asp Phe Asp Leu Asp Val Val Lys Val Ser Lys
1               5                   10                  15

Gln Asp Ser Lys Ile Thr Pro Gln
            20

<210> SEQ ID NO 8
<211> LENGTH: 24
<212> TYPE: PRT
<213> ORGANISM: Bacillus subtilis A1/3

<400> SEQUENCE: 8

Met Ser Lys Phe Asp Asp Phe Asp Leu Asp Val Val Lys Val Ser Lys
1               5                   10                  15

Gln Asp Ser Lys Ile Thr Pro Gln
            20

<210> SEQ ID NO 9
<211> LENGTH: 30
<212> TYPE: PRT
<213> ORGANISM: Staphylococcus epidermidis

<400> SEQUENCE: 9

```
Met Glu Ala Val Lys Glu Lys Asn Asp Leu Phe Asn Leu Asp Val Lys
1               5                   10                  15

Val Asn Ala Lys Glu Ser Asn Asp Ser Gly Ala Glu Pro Arg
            20                  25                  30

<210> SEQ ID NO 10
<211> LENGTH: 30
<212> TYPE: PRT
<213> ORGANISM: Staphylococcus epidermidis strains BN-V1 and BN-V301

<400> SEQUENCE: 10

Met Glu Ala Val Lys Glu Lys Asn Asp Leu Phe Asn Leu Asp Val Lys
1               5                   10                  15

Val Asn Ala Lys Glu Ser Asn Asp Ser Gly Ala Glu Pro Arg
            20                  25                  30

<210> SEQ ID NO 11
<211> LENGTH: 30
<212> TYPE: PRT
<213> ORGANISM: Staphylococcus gallinarum strains

<400> SEQUENCE: 11

Met Glu Ala Val Lys Glu Lys Asn Glu Leu Phe Asp Leu Asp Val Lys
1               5                   10                  15

Val Asn Ala Lys Glu Ser Asn Asp Ser Gly Ala Glu Pro Arg
            20                  25                  30

<210> SEQ ID NO 12
<211> LENGTH: 41
<212> TYPE: PRT
<213> ORGANISM: Streptococcus mutans strains

<400> SEQUENCE: 12

Met Ser Asn Thr Gln Leu Leu Glu Val Leu Gly Thr Glu Thr Phe Asp
1               5                   10                  15

Val Gln Glu Asp Leu Phe Ala Phe Asp Thr Thr Asp Thr Thr Ile Val
            20                  25                  30

Ala Ser Asn Asp Asp Pro Asp Thr Arg
        35                  40

<210> SEQ ID NO 13
<211> LENGTH: 24
<212> TYPE: PRT
<213> ORGANISM: Lactococcus lactis strains

<400> SEQUENCE: 13

Met Lys Glu Gln Asn Ser Phe Asn Leu Leu Gln Glu Val Thr Glu Ser
1               5                   10                  15

Glu Leu Asp Leu Ile Leu Gly Ala
            20

<210> SEQ ID NO 14
<211> LENGTH: 15
<212> TYPE: PRT
<213> ORGANISM: Lactococcus lactis strains

<400> SEQUENCE: 14

Leu Gln Glu Val Thr Glu Ser Glu Leu Asp Leu Ile Leu Gly Ala
1               5                   10                  15

<210> SEQ ID NO 15
```

```
<211> LENGTH: 22
<212> TYPE: PRT
<213> ORGANISM: Kocuria varians strains

<400> SEQUENCE: 15

Met Thr Asn Ala Phe Gln Ala Leu Asp Glu Val Thr Asp Ala Glu Leu
1               5                   10                  15

Asp Ala Ile Leu Gly Gly
            20

<210> SEQ ID NO 16
<211> LENGTH: 26
<212> TYPE: PRT
<213> ORGANISM: Streptococcus mutans T8

<400> SEQUENCE: 16

Met Asn Lys Leu Asn Ser Asn Ala Val Val Ser Leu Asn Glu Val Ser
1               5                   10                  15

Asp Ser Glu Leu Asp Thr Ile Leu Gly Gly
            20                  25

<210> SEQ ID NO 17
<211> LENGTH: 25
<212> TYPE: PRT
<213> ORGANISM: Streptococcus pyogenes strains

<400> SEQUENCE: 17

Met Glu Lys Asn Asn Glu Val Ile Asn Ser Ile Gln Glu Val Ser Leu
1               5                   10                  15

Glu Glu Leu Asp Gln Ile Ile Gly Ala
            20                  25

<210> SEQ ID NO 18
<211> LENGTH: 29
<212> TYPE: PRT
<213> ORGANISM: Streptococcus salivarius 20P3

<400> SEQUENCE: 18

Met Asn Ala Met Lys Asn Ser Lys Asp Ile Leu Asn Asn Ala Ile Glu
1               5                   10                  15

Glu Val Ser Glu Lys Glu Leu Met Glu Val Ala Gly Gly
            20                  25

<210> SEQ ID NO 19
<211> LENGTH: 19
<212> TYPE: PRT
<213> ORGANISM: Bacillus subtilis 168

<400> SEQUENCE: 19

Met Glu Lys Leu Phe Lys Glu Val Lys Leu Glu Glu Leu Glu Asn Gln
1               5                   10                  15

Lys Gly Ser

<210> SEQ ID NO 20
<211> LENGTH: 31
<212> TYPE: PRT
<213> ORGANISM: Lactobacillus sake L45

<400> SEQUENCE: 20

Met Lys Thr Glu Lys Lys Val Leu Asp Glu Leu Ser Leu His Ala Ser
1               5                   10                  15

Ala Lys Met Gly Ala Arg Asp Val Glu Ser Ser Met Asn Ala Asp
```

<210> SEQ ID NO 21
<211> LENGTH: 23
<212> TYPE: PRT
<213> ORGANISM: Ruminococcus gnavus strains

<400> SEQUENCE: 21

Met Arg Asn Asp Val Leu Thr Leu Thr Asn Pro Met Glu Glu Lys Glu
1               5                   10                  15

Leu Glu Gln Ile Leu Gly Gly
            20

<210> SEQ ID NO 22
<211> LENGTH: 23
<212> TYPE: PRT
<213> ORGANISM: Butyrivibrio fibrisolvens AR10

<400> SEQUENCE: 22

Met Asn Lys Glu Leu Asn Ala Leu Thr Asn Pro Ile Asp Glu Lys Glu
1               5                   10                  15

Leu Glu Gln Ile Leu Gly Gly
            20

<210> SEQ ID NO 23
<211> LENGTH: 25
<212> TYPE: PRT
<213> ORGANISM: Streptococcus pyogenes M type 49

<400> SEQUENCE: 23

Met Thr Lys Glu His Glu Ile Ile Asn Ser Ile Gln Glu Val Ser Leu
1               5                   10                  15

Glu Glu Leu Asp Gln Ile Ile Gly Ala
            20                  25

<210> SEQ ID NO 24
<211> LENGTH: 24
<212> TYPE: PRT
<213> ORGANISM: Lactococcus lactis subsp. cremoris J46

<400> SEQUENCE: 24

Met Lys Glu Gln Asn Ser Phe Asn Leu Leu Gln Glu Val Thr Glu Ser
1               5                   10                  15

Glu Leu Asp Leu Ile Leu Gly Ala
            20

<210> SEQ ID NO 25
<211> LENGTH: 26
<212> TYPE: PRT
<213> ORGANISM: Streptococcus pyogenes T11 (M type 4)

<400> SEQUENCE: 25

Met Lys Asn Ser Lys Asp Ile Leu Thr Asn Ala Thr Glu Glu Val Ser
1               5                   10                  15

Glu Lys Glu Leu Met Glu Val Ala Gly Gly
            20                  25

<210> SEQ ID NO 26
<211> LENGTH: 23
<212> TYPE: PRT
<213> ORGANISM: Streptococcus pyogenes strains

<400> SEQUENCE: 26

Met Asn Asn Thr Ile Lys Asp Phe Asp Leu Asp Leu Lys Thr Asn Lys
1               5                   10                  15

Lys Asp Thr Ala Thr Pro Tyr
            20

<210> SEQ ID NO 27
<211> LENGTH: 25
<212> TYPE: PRT
<213> ORGANISM: Streptococcus bovis HJ50

<400> SEQUENCE: 27

Met Met Asn Ala Thr Glu Asn Gln Ile Phe Val Glu Thr Val Ser Asp
1               5                   10                  15

Gln Glu Leu Glu Met Leu Ile Gly Gly
            20                  25

<210> SEQ ID NO 28
<211> LENGTH: 30
<212> TYPE: PRT
<213> ORGANISM: Lactobacillus plantarum strains

<400> SEQUENCE: 28

Met Lys Ile Ser Lys Ile Glu Ala Gln Ala Arg Lys Asp Phe Phe Lys
1               5                   10                  15

Lys Ile Asp Thr Asn Ser Asn Leu Leu Asn Val Asn Gly Ala
            20                  25                  30

<210> SEQ ID NO 29
<211> LENGTH: 29
<212> TYPE: PRT
<213> ORGANISM: Lactococcus lactis IFPL3593

<400> SEQUENCE: 29

Met Asn Lys Asn Glu Ile Glu Thr Gln Pro Val Thr Trp Leu Glu Glu
1               5                   10                  15

Val Ser Asp Gln Asn Phe Asp Glu Asp Val Phe Gly Ala
            20                  25

<210> SEQ ID NO 30
<211> LENGTH: 32
<212> TYPE: PRT
<213> ORGANISM: Staphylococcus aureus C55

<400> SEQUENCE: 30

Met Lys Ser Ser Phe Leu Glu Lys Asp Ile Glu Glu Gln Val Thr Trp
1               5                   10                  15

Phe Glu Glu Val Ser Glu Gln Glu Phe Asp Asp Asp Ile Phe Gly Ala
            20                  25                  30

<210> SEQ ID NO 31
<211> LENGTH: 35
<212> TYPE: PRT
<213> ORGANISM: Lactobacillus plantarum strains

<400> SEQUENCE: 31

Met Thr Lys Thr Ser Arg Arg Lys Asn Ala Ile Ala Asn Tyr Leu Glu
1               5                   10                  15

Pro Val Asp Glu Lys Ser Ile Asn Glu Ser Phe Gly Ala Gly Asp Pro
            20                  25                  30

Glu Ala Arg
        35

<210> SEQ ID NO 32
<211> LENGTH: 36
<212> TYPE: PRT
<213> ORGANISM: Lactococcus lactis IFPL3593

<400> SEQUENCE: 32

Met Lys Glu Lys Asn Met Lys Lys Asn Asp Thr Ile Glu Leu Gln Leu
1               5                   10                  15

Gly Lys Tyr Leu Glu Asp Asp Met Ile Glu Leu Ala Glu Gly Asp Glu
            20                  25                  30

Ser His Gly Gly
        35

<210> SEQ ID NO 33
<211> LENGTH: 35
<212> TYPE: PRT
<213> ORGANISM: Staphylococcus aureus C55

<400> SEQUENCE: 33

Met Lys Asn Glu Leu Gly Lys Phe Leu Glu Glu Asn Glu Leu Glu Leu
1               5                   10                  15

Gly Lys Phe Ser Glu Ser Asp Met Leu Glu Ile Thr Asp Asp Glu Val
            20                  25                  30

Tyr Ala Ala
        35

<210> SEQ ID NO 34
<211> LENGTH: 30
<212> TYPE: PRT
<213> ORGANISM: Enterococcus faecalis strains

<400> SEQUENCE: 34

Met Glu Asn Leu Ser Val Val Pro Ser Phe Glu Glu Leu Ser Val Glu
1               5                   10                  15

Glu Met Glu Ala Ile Gln Gly Ser Gly Asp Val Gln Ala Glu
            20                  25                  30

<210> SEQ ID NO 35
<211> LENGTH: 42
<212> TYPE: PRT
<213> ORGANISM: Enterococcus faecalis strains

<400> SEQUENCE: 35

Met Leu Asn Lys Glu Asn Gln Glu Asn Tyr Tyr Ser Asn Lys Leu Glu
1               5                   10                  15

Leu Val Gly Pro Ser Phe Glu Glu Leu Ser Leu Glu Glu Met Glu Ala
            20                  25                  30

Ile Gln Gly Ser Gly Asp Val Gln Ala Glu
        35                  40

<210> SEQ ID NO 36
<211> LENGTH: 59
<212> TYPE: PRT
<213> ORGANISM: Streptomyces cinnamoneus cinnamoneus DSM 40005

<400> SEQUENCE: 36

Met Thr Ala Ser Ile Leu Gln Gln Ser Val Val Asp Ala Asp Phe Arg
1               5                   10                  15

Ala Ala Leu Leu Glu Asn Pro Ala Ala Phe Gly Ala Ser Ala Ala Ala
            20                  25                  30

```
Leu Pro Thr Pro Val Glu Ala Gln Asp Gln Ala Ser Leu Asp Phe Trp
        35                  40                  45

Thr Lys Asp Ile Ala Ala Thr Glu Ala Phe Ala
    50                  55

<210> SEQ ID NO 37
<211> LENGTH: 48
<212> TYPE: PRT
<213> ORGANISM: Bacillus sp. strain HIL Y-85,54728

<400> SEQUENCE: 37

Met Ser Gln Glu Ala Ile Ile Arg Ser Trp Lys Asp Pro Phe Ser Arg
1               5                   10                  15

Glu Asn Ser Thr Gln Asn Pro Ala Gly Asn Pro Phe Ser Glu Leu Lys
            20                  25                  30

Glu Ala Gln Met Asp Lys Leu Val Gly Ala Gly Asp Asn Glu Ala Ala
        35                  40                  45

<210> SEQ ID NO 38
<211> LENGTH: 10
<212> TYPE: PRT
<213> ORGANISM: Artificial
<220> FEATURE:
<223> OTHER INFORMATION: Description of the Artificial Sequence:
      Leader peptide

<400> SEQUENCE: 38

Leu Glu Glu Val Ser Glu Gln Glu Leu Asp
1               5                   10

<210> SEQ ID NO 39
<211> LENGTH: 6
<212> TYPE: PRT
<213> ORGANISM: Artificial
<220> FEATURE:
<223> OTHER INFORMATION: Description of the Artificial Sequence:
      Leader peptide

<400> SEQUENCE: 39

Leu Phe Asp Leu Asp Leu
1               5

<210> SEQ ID NO 40
<211> LENGTH: 5
<212> TYPE: PRT
<213> ORGANISM: Artificial
<220> FEATURE:
<223> OTHER INFORMATION: Description of the Artificial Sequence:
      Leader peptide

<400> SEQUENCE: 40

Phe Asn Leu Asp Val
1               5

<210> SEQ ID NO 41
<211> LENGTH: 5
<212> TYPE: PRT
<213> ORGANISM: Artificial
<220> FEATURE:
<223> OTHER INFORMATION: Description of the Artificial Sequence:
      Part of nisin leader peptide

<400> SEQUENCE: 41

Arg Ala Ser Val Ala
1               5
```

<210> SEQ ID NO 42
<211> LENGTH: 5
<212> TYPE: PRT
<213> ORGANISM: Artificial
<220> FEATURE:
<223> OTHER INFORMATION: Description of the Artificial Sequence:
    Part of nisin leader peptide
<220> FEATURE:
<221> NAME/KEY: MISC_FEATURE
<222> LOCATION: (3)..(3)
<223> OTHER INFORMATION: Dehydroalanine (dehydrated Serine)

<400> SEQUENCE: 42

Arg Ala Ala Val Ala
1               5

<210> SEQ ID NO 43
<211> LENGTH: 10
<212> TYPE: PRT
<213> ORGANISM: Artificial
<220> FEATURE:
<223> OTHER INFORMATION: Description of the Artificial Sequence:
    Part of nisin leader peptide

<400> SEQUENCE: 43

Ile Thr Ser Ile Ser Arg Ala Ser Val Ala
1               5                   10

<210> SEQ ID NO 44
<211> LENGTH: 60
<212> TYPE: PRT
<213> ORGANISM: Artificial
<220> FEATURE:
<223> OTHER INFORMATION: Description of the Artificial Sequence:
    peptide encoded by pNGnisB

<400> SEQUENCE: 44

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Met Ser Thr Lys Asp
            20                  25                  30

Phe Asn Leu Asp Leu Val Ser Val Ser Lys Lys Asp Ser Gly Ala Ser
        35                  40                  45

Pro Arg Ile Thr Ser Ile Ser Arg Ala Ser Val Ala
    50                  55                  60

<210> SEQ ID NO 45
<211> LENGTH: 7
<212> TYPE: PRT
<213> ORGANISM: Artificial
<220> FEATURE:
<223> OTHER INFORMATION: Description of the Artificial Sequence:
    N-terminal leader extension

<400> SEQUENCE: 45

Met Asp Thr Tyr Arg Tyr Ile
1               5

<210> SEQ ID NO 46
<211> LENGTH: 7
<212> TYPE: PRT
<213> ORGANISM: Artificial
<220> FEATURE:
<223> OTHER INFORMATION: Description of the Artificial Sequence:
    Consensus motif TAT-specific export signal
<220> FEATURE:

-continued

```
<221> NAME/KEY: VARIANT
<222> LOCATION: (1)..(1)
<223> OTHER INFORMATION: Thr
<220> FEATURE:
<221> NAME/KEY: MISC_FEATURE
<222> LOCATION: (4)..(4)
<223> OTHER INFORMATION: Any amino acid

<400> SEQUENCE: 46

Ser Arg Arg Xaa Phe Leu Lys
1               5

<210> SEQ ID NO 47
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (10)..(10)
<223> OTHER INFORMATION: AMIDATION
<220> FEATURE:
<223> OTHER INFORMATION: Description of the Artificial Sequence:
      LHRH

<400> SEQUENCE: 47

Glu His Trp Ser Tyr Gly Leu Arg Pro Gly
1               5                   10

<210> SEQ ID NO 48
<211> LENGTH: 10
<212> TYPE: PRT
<213> ORGANISM: Artificial
<220> FEATURE:
<223> OTHER INFORMATION: Description of the Artificial Sequence:
      LHRH variant

<400> SEQUENCE: 48

Gln His Trp Ser Tyr Gly Cys Arg Pro Gly
1               5                   10

<210> SEQ ID NO 49
<211> LENGTH: 10
<212> TYPE: PRT
<213> ORGANISM: Artificial
<220> FEATURE:
<223> OTHER INFORMATION: Description of the Artificial Sequence:
      LHRH variant

<400> SEQUENCE: 49

Gln His Trp Ser Tyr Ser Leu Arg Cys Gly
1               5                   10

<210> SEQ ID NO 50
<211> LENGTH: 13
<212> TYPE: PRT
<213> ORGANISM: Artificial
<220> FEATURE:
<223> OTHER INFORMATION: Description of the Artificial Sequence:
      Part of epo peptide

<400> SEQUENCE: 50

Tyr Ala Ser His Phe Gly Pro Leu Gly Trp Val Cys Lys
1               5                   10

<210> SEQ ID NO 51
```

```
<211> LENGTH: 63
<212> TYPE: PRT
<213> ORGANISM: Artificial
<220> FEATURE:
<223> OTHER INFORMATION: Description of the Artificial Sequence:
      Peptide encoded by pLPepo

<400> SEQUENCE: 51

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Met Ser Thr Lys Asp
            20                  25                  30

Phe Asn Leu Asp Leu Val Ser Val Ser Lys Lys Asp Ser Gly Ala Ser
        35                  40                  45

Pro Arg Tyr Ala Ser His Phe Gly Pro Leu Gly Trp Val Cys Lys
    50                  55                  60

<210> SEQ ID NO 52
<211> LENGTH: 60
<212> TYPE: PRT
<213> ORGANISM: Artificial
<220> FEATURE:
<223> OTHER INFORMATION: Description of the Artificial Sequence:
      Nisin leader with sec signal

<400> SEQUENCE: 52

Met Ser Thr Lys Asp Phe Asn Leu Asp Leu Val Ser Val Ser Lys Lys
1               5                   10                  15

Asp Ser Gly Ala Ser Pro Arg Met Lys Lys Lys Ile Ile Ser Ala Ile
            20                  25                  30

Leu Met Ser Thr Val Ile Leu Ser Ala Ala Ala Pro Leu Ser Gly Val
        35                  40                  45

Tyr Ala Ile Thr Ser Ile Ser Arg Ala Ser Val Ala
    50                  55                  60

<210> SEQ ID NO 53
<211> LENGTH: 10
<212> TYPE: PRT
<213> ORGANISM: Artificial
<220> FEATURE:
<223> OTHER INFORMATION: Description of the Artificial Sequence:
      Consensus leader peptide
<220> FEATURE:
<221> NAME/KEY: MISC_FEATURE
<222> LOCATION: (1)..(1)
<223> OTHER INFORMATION: Xaa can be any hydrophobic amino acid
<220> FEATURE:
<221> NAME/KEY: VARIANT
<222> LOCATION: (2)..(2)
<223> OTHER INFORMATION: Glu
<220> FEATURE:
<221> NAME/KEY: VARIANT
<222> LOCATION: (4)..(4)
<223> OTHER INFORMATION: Leu
<220> FEATURE:
<221> NAME/KEY: VARIANT
<222> LOCATION: (5)..(5)
<223> OTHER INFORMATION: Thr
<220> FEATURE:
<221> NAME/KEY: VARIANT
<222> LOCATION: (6)..(6)
<223> OTHER INFORMATION: Glu
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: VARIANT
<222> LOCATION: (10)..(10)
```

```
<223> OTHER INFORMATION: Glu

<400> SEQUENCE: 53

Xaa Asp Glu Val Ser Asp Xaa Glu Leu Asp
1               5                   10

<210> SEQ ID NO 54
<211> LENGTH: 5
<212> TYPE: PRT
<213> ORGANISM: Artificial
<220> FEATURE:
<223> OTHER INFORMATION: Description of the Artificial Sequence:
      Consensus leader peptide
<220> FEATURE:
<221> NAME/KEY: VARIANT
<222> LOCATION: (2)..(2)
<223> OTHER INFORMATION: Glu or Asn
<220> FEATURE:
<221> NAME/KEY: VARIANT
<222> LOCATION: (5)..(5)
<223> OTHER INFORMATION: Ile or Val

<400> SEQUENCE: 54

Phe Asp Leu Asp Leu
1               5

<210> SEQ ID NO 55
<211> LENGTH: 19
<212> TYPE: PRT
<213> ORGANISM: Artificial
<220> FEATURE:
<223> OTHER INFORMATION: Description of the Artificial Sequence:
      consensus leader peptide
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any amino acid
<220> FEATURE:
<221> NAME/KEY: MISC_FEATURE
<222> LOCATION: (15)..(15)
<223> OTHER INFORMATION: Xaa can be any amino acid

<400> SEQUENCE: 55

Leu Xaa Asn Ser Leu Glu Glu Val Ser Glu Xaa Glu Leu Asp Xaa Ile
1               5                   10                  15

Leu Gly Gly

<210> SEQ ID NO 56
<211> LENGTH: 19
<212> TYPE: PRT
<213> ORGANISM: Artificial
<220> FEATURE:
<223> OTHER INFORMATION: Description of the Artificial Sequence:
      Consensus leader peptide
<220> FEATURE:
<221> NAME/KEY: MISC_FEATURE
<222> LOCATION: (7)..(18)
<223> OTHER INFORMATION: Xaa can be any aminoacid sequence

<400> SEQUENCE: 56

Leu Phe Asp Leu Asp Leu Xaa Xaa Xaa Xaa Xaa Xaa Xaa Xaa Xaa
1               5                   10                  15

Xaa Xaa Glu

<210> SEQ ID NO 57
```

```
<211> LENGTH: 32
<212> TYPE: DNA
<213> ORGANISM: Artificial
<220> FEATURE:
<223> OTHER INFORMATION: Description of the Artificial Sequence:
      primer

<400> SEQUENCE: 57
tcggtctctc atggcatacg acagtcgttt tg                               32

<210> SEQ ID NO 58
<211> LENGTH: 33
<212> TYPE: DNA
<213> ORGANISM: Artificial
<220> FEATURE:
<223> OTHER INFORMATION: Description of the Artificial Sequence:
      primer

<400> SEQUENCE: 58
aaagtactag catttacttc aaaggcccca acc                              33

<210> SEQ ID NO 59
<211> LENGTH: 34
<212> TYPE: DNA
<213> ORGANISM: Artificial
<220> FEATURE:
<223> OTHER INFORMATION: Description of the Artificial Sequence:
      primer

<400> SEQUENCE: 59
gcgaagacgc catgagcgat gaacagaaaa agcc                             34

<210> SEQ ID NO 60
<211> LENGTH: 27
<212> TYPE: DNA
<213> ORGANISM: Artificial
<220> FEATURE:
<223> OTHER INFORMATION: Description of the Artificial Sequence:
      primer

<400> SEQUENCE: 60
aaagtactac gcagtctgaa caagcgg                                     27

<210> SEQ ID NO 61
<211> LENGTH: 36
<212> TYPE: DNA
<213> ORGANISM: Artificial
<220> FEATURE:
<223> OTHER INFORMATION: Description of the Artificial Sequence:
      primer

<400> SEQUENCE: 61
ttagtactaa agattttaac ttggatttgg tatctg                           36

<210> SEQ ID NO 62
<211> LENGTH: 29
<212> TYPE: DNA
<213> ORGANISM: Artificial
<220> FEATURE:
<223> OTHER INFORMATION: Description of the Artificial Sequence:
      primer

<400> SEQUENCE: 62
gcaatatcag taattgcttt atcaactgc                                   29

<210> SEQ ID NO 63
<211> LENGTH: 31
```

```
<212> TYPE: DNA
<213> ORGANISM: Artificial
<220> FEATURE:
<223> OTHER INFORMATION: Description of the Artificial Sequence:
      primer

<400> SEQUENCE: 63
aaagaattcc ctgttactgg agatggagaa g                                    31

<210> SEQ ID NO 64
<211> LENGTH: 34
<212> TYPE: DNA
<213> ORGANISM: Artificial
<220> FEATURE:
<223> OTHER INFORMATION: Description of the Artificial Sequence:
      primer

<400> SEQUENCE: 64
aaacccgggc aattttcaga atctattcag aaac                                 34

<210> SEQ ID NO 65
<211> LENGTH: 5
<212> TYPE: PRT
<213> ORGANISM: Artificial
<220> FEATURE:
<223> OTHER INFORMATION: Description of the Artificial Sequence:
      first five nisin propeptide residues

<400> SEQUENCE: 65

Ile Thr Ser Ile Ser
1               5
```

METHODS FOR THE PRODUCTION AND SECRETION OF MODIFIED PEPTIDES

The invention relates to the production of heterologous polypeptides in a recombinant host cell. More specifically, it relates to the production and secretion of peptides, such as biologically active peptides, that are modified by one or more lantibiotic-synthesizing enzymes, in particular by the dehydratase LanB.

A wide spectrum of peptides is known that are biologically active, such as hormones, growth factors, enzyme inhibitors, antigens, antibiotics and ionophores. Cyclization of peptides has been shown to be a valuable method to obtain stable analogs of, among others, bioactive peptides. Furthermore, by conformational constraints, an enhanced or modulated interaction between a peptide and its binding partner (e.g. a receptor or enzyme) can be obtained (Li et al. (2002) Curr. Top. Med. Chem. 2, 325; Ösapay et al. (1997) J. Med. Chem. 40, 2241; Rew Y. et al. (2002) J. Med. Chem. 45, 3746-3754). Thioether rings can contribute to enhanced peptide stability, enhanced resistance against proteolytic degradation (Bierbaum et al. (1996) Appl. Environm. Microbiol. 62, 385; Van der Meer et al. (1993) J. Bacteriol. 175, 2578) and modulation of receptor interaction (Ösapay et al. (1997) J. Med. Chem. 40, 2241).

Lantibiotics are bacterial peptides with intramolecular thioether rings. They owe their name to antibiotic activities, that most of them have, and the presence of lanthionine residues, which are thioether-containing amino acids. Lantibiotics are produced by, and primarily act on, Gram-positive bacteria (for review see Chatterjee, C., et al. (2005) *Chem Rev* 105, 633-684.

Lantibiotics originate from ribosomally synthesised prepeptides that are post-translationally modified to result in (methyl)lanthionine- and/or dehydroresidue-containing peptides. Dehydroalanine and dehydrobutyrine result from lantibiotic enzyme-mediated dehydration of serine and threonine, respectively. Intramolecular thioether bridges or rings formed by the thioether amino acids lanthionine (Lan) and 3-methyllanthionine (MeLan) result from lantibiotic enzyme-mediated coupling of a dehydroresidue to a cysteine.

Well known lantibiotics include subtilin and the food preservative nisin, whose structure is very similar. Thioether rings protect lantibiotics against proteolytic degradation. For instance, the lantibiotic nisin remains active after trypsin treatment. Thioether rings are essential for some lantibiotic activities. Opening of the thioether ring A or C in nisin causes deletion of the membrane permeabilization capacity. Ring A of nisin is necessary for its capacity to autoinduce its own synthesis and for nisin's capacity to block the peptidoglycan synthesis of bacteria by interacting with lipid II. It is essential in these cases to have thioether rings and not disulfide rings, since replacement of thioether rings by disulfide bridges leads to loss of antimicrobial activity.

Given the fact that thioether rings can contribute to the stability and activity of bioactive peptides, it has been proposed that the lantibiotic-synthesizing enzymes can be advantageously used to introduce thioether rings in peptides that normally do not contain a thioether bridge, to improve the stability of the peptide and/or to alter its activity (Kuipers et al. 2004. J. Biol. Chem. 279, 22176-22182).

Lantibiotic-synthesizing enzymes have been described as being organized in a membrane-bound complex (Siegers et al. 1996. J. Biol. Chem. 271, 12294-12301; Kiesau et al. 1997. J. Bacteriol. 179, 1475-1481; Sahl et al. 1998. Annu. Rev. Microbiol. 52:41-7). This complex is composed of the lantibiotic transporter (LanT), the dehydrating enzyme (LanB; also referred to as dehydratase) and the cyclase (LanC). In the case of some lantibiotics a bifunctional enzyme (LanM) performs both the dehydration and the cyclization steps. The N-terminal lantibiotic leader peptide in the ribosomally synthesized prepropeptides is a recognition signal for the lantibiotic enzymes, starting with the dehydrating enzyme or the enzyme which performs both dehydration and ring formation. It is thought that the leader peptide binds to the lantibiotic complex to bring the prepropeptide in close proximity of the lantibiotic enzymes. The enzyme complexes suggest that it is necessary that the dehydrating and ring forming enzymes are attached to the transporter because a lantibiotic prepropeptide would otherwise be exported without undergoing modification or, alternatively, a modified peptide would accumulate in the cell.

In most cases, translocation of the lantibiotic depends entirely on the dedicated lantibiotic transporter. Disruption of the nisin transporter (NisT) was shown to cause accumulation of fully modified prenisin inside the cells (Qiao et al. 1996. FEMS Microbiol. Lett. 144, 89-93). Kuipers et al previously showed that the lantibiotic transporter NisT can excrete unmodified lantibiotics and fusions of the leader peptide with non-lantibiotic peptides and that the combination of a dehydrating enzyme and the lantibiotic transporter, in the absence of the cyclase, is also functional (Kuipers et al. 2004. J. Biol. Chem. 279, 22176-22182).

The common understanding is that peptides that are modified by the lantibiotic enzyme complex are translocated by the also in the complex available dedicated lantibiotic transporter. However, alternative ways of processing the formation and secretion of lanthionine-bridge-containing peptides without the requirement of the intact complex would be desirable, inter alia for the recombinant production of biologically active peptides.

The invention now surprisingly shows that a peptide of interest can be dehydrated in a host cell by an isolated lantibiotic dehydratase, such as LanB, which thus is not part of the conventional lantibiotic enzyme complex, and that this modified peptide can be secreted by a protein export system other than the dedicated lantibiotic transporters. Furthermore the invention shows that LanBC, in the absence of (disrupted) LanT, can dehydrate and cyclize. This is achieved by the construction of a polypeptide comprising a peptide of interest preceded by a lantibiotic leader peptide and a non-lantibiotic export signal.

Provided is a nucleic acid construct encoding a polypeptide comprising 1) a non-lantibiotic export signal that is recognized by a non-lantibiotic export system; 2) a lantibiotic leader peptide that is recognized by a lantibiotic dehydratase and, C-terminally of said export signal and said leader peptide, 3) a peptide of interest containing one or more serine or threonine residue(s) which can be posttranslationally dehydrated by said dehydratase.

Expression of such a construct in a suitable host cell comprising the necessary dehydratase and non-lantibiotic export system is advantageously used in the recombinant production of modified peptides with novel bioactivities and/or improved stability. Thus, in contrast to conventional lantibiotics wherein the LanBCT complex is responsible for both the modification and export of the peptide, the invention demonstrates a) that LanB and LanBC can function independently from the BTC complex and b) that the modified peptide can be exported by a non-lantibiotic export system. It is unlikely that this alternative export system forms a complex together with the dehydrating and, if present, ring forming enzymes. It is therefore surprising that a polypeptide that is recognized and modified by a lantibiotic enzyme can be targeted to a non-lantibiotic export system.

A polypeptide encoded by a nucleic acid of the invention comprises a lantibiotic leader peptide that allows for the recognition of the peptide by a dehydratase, and preferably also by a cyclase that can form a lanthionine-bridge. In one embodiment, a leader peptide in a polypeptide of the invention bears a lantibiotic leader consensus motif that can be derived from the amino acid sequence alignment of known lantibiotic leader peptides. Amino acid sequences of lantibiotic leader peptides are available from public databases. Tables 1A and 1B show exemplary alignments of lantibiotic leader peptides. A skilled person will be able to derive a consensus motif from the aligned sequences, for instance using publicly or commercially available alignment software such as AlignX of Vector NTI. AlignX performs multiple sequence alignments on both protein and nucleic acid sequences uses using the ClustalW algorithm. It plots homology, sequence complexity, phylogenetic trees, and dot-matrix homology plots. AlignX accepts standard, feature-rich, text files of sequence, such as GenBank, EMBL and GenPept files. On one embodiment, the consensus motif is derived from the sequences in Table 1 using the ClustalW algorithm. It is preferred that a leader peptide consensus motif is derived from an alignment of at least 5, more preferably at least 10, most preferably at least 15 known leader peptide sequences. The thus obtained consensus motif can subsequently be verified for leader peptide activity, i.e. recognition by a lantibiotic dehydratase and serine or threonine dehydration, using methods disclosed herein. For instance, the procedure of Example 1 herein below can be followed with the modification that the leader peptide sequence to be verified is cloned into the pNG411TPPII to replace the nisin leader sequence. Dehydration of the sequence ITSISRASVA (SEQ ID NO:43) can be monitored using Maldi-TOF MS.

The leader peptide consensus sequence can comprise the consensus motif X1-D/E-E-V/L-S/T-D/E-X2-E-L-D/E (SEQ ID NO:53), wherein X1 is any hydrophobic amino acid and wherein X2 is any amino acid. For example, it comprises the sequence LEEVSEQELD (SEQ ID NO:38). In another embodiment, a leader peptide comprises a consensus motif F-D/E/N-L-D-X3 (SEQ ID NO:54), wherein X3 is L, I or V. For example, it comprises the sequence LFDLDL (SEQ ID NO:39) or FNLDV (SEQ ID NO:40).

On the other hand, it has been reported for the lantibiotics mutacin (Chen P et al. FEMS Microbiol Lett. 2001; 195(2): 139), Pep5 (Neis S et al. FEMS Microbiol Lett. 1997; 149(2): 249) and nisin (Van der Meer et al (1994) *J. Biol. Chem.* 269, 3555-3562.) that some of the conserved leader peptide residues are essential for the lantibiotic biosynthesis, whereas other residues are important for optimal biosynthesis rates.

In a preferred embodiment, a polypeptide provided herein comprises the leader peptide of a lantibiotic, for example the leader peptide of a lantibiotic selected from the group consisting of nisin A, nisin Z, subtilin, ericin S, ericin A, streptin, epidermin, val1-leu6-epidermin, gallidermin, mutacin 1140, mutacin B-Ny266, mutacin III, mutacin I, pep5, epilancin K7, epicidin 280, lacticin 481, variacin, mutacin II, streptococcin A-FF22, salivaricin A, lactocin S, cypemycin, plantaricin C, actagardine, Ala(0)-actagardine, lacticin 3147A1, lacticin 3147A2, staphylococcin C55α, staphylococcin C55b, plantaricin Wa, plantaricin Wb, cytolysin Ll, cytolysin Ls, ruminococcin A, carnocin U149, macedocin, bovicin HJ50, nukacin ISK-1, sublancin 168, butyrivibriocin OR79A, cinnamycin, duramycin, ancovenin, mersacidin, sapB (see Table 2), or a homolog of any of these leader peptides that allows for recognition and modification of the downstream located peptide of interest by the desired lantibiotic-modifying enzyme(s). The homolog shows at least 70%, preferably at least 80%, more preferably at least 90%, like 92%, 95% or even 98% sequence identity to the sequence one of the leader peptide sequences shown in Tables 1 and 2.

For example, the leader peptide can be a truncated or mutated lantibiotic leader peptide that is still capable of inducing post-translational modification of the peptide of interest. The leader does not need to have the capacity to induce translocation by a lantibiotic transporter like LanT, since this function is taken over by the non-lantibiotic export signal that is present in the polypeptide of the invention.

In a specific aspect the leader peptide is the nisin leader peptide or a truncated or mutated version thereof wherein up to 4 amino acids at the N-terminus and/or wherein any one up to 5 amino acids at the C-terminus is mutated.

According to the invention, the lantibiotic leader peptide located upstream of the amino acid residue(s) in the protein of interest to be modified allows for recognition by at least a lantibiotic dehydratase and subsequent dehydration of the residue. To ensure that the dehydratase indeed has access to the residue(s) to be modified, the distance between the leader peptide and the residue(s) to be modified should not be too large. However, a stretch of a few (e.g. 2-10) amino acid residues in between the leader peptide and the peptide of interest may enhance export of the peptide.

A polypeptide of the invention comprises a lantibiotic leader peptide that is recognized by at least a dehydratase such that at least one serine or threonine residue of the peptide of interest is post-translationally dehydrated in a host cell that comprises said dehydratase and expresses said polypeptide. As will be shown below, the dehydrated polypeptide can be targeted to a non-lantibiotic export system of the host cell by a non-lantibiotic export signal. Some of the export systems are also signal peptidases which cleave off the export signal.

In any case, a leader peptide and export signal, if present, can be removed from the modified peptide following secretion. Depending on the amino acid sequence, a peptide can be treated with a protease to remove a leader peptide and/or a non-lantibiotic export signal. For example, the nisin leader sequence ends with an arginine residue and can thus be removed with trypsin. Specific cleavage sites can be engineered in the C-terminus of the leader peptide without interfering with LanB or LanC action. In that case particularly useful proteases include thrombin and enterokinase. Other proteases that can be used are: lysC, Arg C, Asp N, Glu C and chymotrypsin. Chemical cleavage is also encompassed, for instance using CNBr-cleavage after a methionine residue. A cleavage site for a protease or chemical reagent can of course be introduced at any desired site of the polypeptide of the invention, using e.g. site-directed mutagenesis.

Preferably, the dehydratase is LanB or LanM, for example a dehydratase selected from the group consisting of, NisB, EpiB, SpaB and PepB. As a result, the—at least one—serine or threonine residue in the peptide of interest is converted into a dehydroalanine or dehydrobutyrine, respectively.

In one embodiment, said lantibiotic leader peptide is not only recognized by a dehydratase but also by a cyclase (LanC), which is a lantibiotic-synthesizing enzyme catalysing the cyclization or coupling of a dehydroresidue to a cysteine. Preferably, the cyclase is selected from the group consisting of N is C, EpiC, SpaC and PepC. Because a peptide of interest comprises, in addition to a serine or threonine residue, at least one cysteine residue which can be coupled to a dehydrated serine or threonine residue, this can yield a (methyl)lanthionine-containing peptide of interest. The cysteines can be located either N- or C-terminally from the serine or threonine residue(s). Preferably, the cysteines are separated up to 20 amino acids, preferably up to 10, more preferably up to 5 amino acids, from the serine or threonine residue to be modified. As said, such thioether-bridges can be used to confer increased (bio)stability to a peptide, and. it may as well affect the biological activity of the peptide.

In one embodiment, both the dehydration and the cyclization steps are performed within the host cell. Of course, the host cell expressing the polypeptide should. in that case also contain a cyclase, the enzyme that catalyses the cyclization step. Like the dehydratase, the host cell can naturally contain an endogenous cyclase enzyme, or the cyclase can be expressed by transforming the host cell with an expressible construct coding for a (heterologous) cyclase enzyme. However, it is also possible to first isolate a peptide that is dehydrated (or a mixture of dehydrated peptides that is partially cyclized) by a host cell and subsequently induce ring formation in vitro. In vitro cyclase activity of lacticin M has been demonstrated by the group of van der Donk (Xie, L., et al. (2004) Science 303, 679-681; patent: US2005/0164339 A1, van der Donk et al). In one embodiment, a dehydrated peptide is treated in vitro with a cyclase. To allow for recognition of the secreted, dehydrated peptide by the cyclase it is preferred that the peptide still comprises a lantibiotic leader. Therefore, if in vitro cyclization of a dehydrated peptide is desired, the peptide should be encoded by a nucleic acid which also codes for an internal rather than an N-terminal leader peptide sequence. Otherwise, i.e. in case of an N-terminal leader peptide, the leader peptide will be cleaved off together with the internal export signal by the leader peptidase following translocation of the peptide. In another embodiment, cyclization of a dehydrated peptide is performed outside the cells not by the lantibiotic cyclase but by non-enzymatic means, preferably by incubation at pH 8.0 for one hour. (Okeley et al. 2000 Org. Lett. 2, 3603-3606; Burrage et al. 2000. Chem. Eur. J. 6, 1455-1466).

According to the invention, the non-lantibiotic export signal present in a polypeptide according to the invention is a signal for an export system that translocates peptides across a lipid bilayer of a host cell. Preferably, said non-lantibiotic export system has a broad substrate specificity. This allows for the export of a wide range of different peptides, including peptides with a (locally) constraint structure such as those containing one or more thioether rings.

In one embodiment, the non-lantibiotic export signal is a signal for the Sec-dependent secretion system. The Sec (which stands for secretion) system is considered to be the most important protein export pathway as most proteins use this system and it is present in all organisms studied so far. The system is comprised of several components that have been characterized most extensively in Escherichia coli. The Sec-system in E. coli is made up of the proteins SecA, SecB, SecD, SecE, SecF, SecG, SecY, YajC, and YidC. SecA recognizes a specific N-terminal signal sequence and targets the precursor to the SecYEG translocon for transport. SecB, a cytoplasmic chaperone, keeps the precursor in a translocation-competent conformation and interacts with the C-terminus of SecA. After the targeting and translocation steps have occurred, the secretory pre-protein is then released from the SecYEG pore and is tethered to the membrane via its signal peptide. Type I signal peptidase (SPase), an essential membrane-bound endopeptidase, functions to cleave off the signal peptide releasing the secretory protein to its final destination. In one embodiment of the invention, a polypeptide comprises an N-terminal signal sequence that is recognized by the SecA protein of the Sec-system, to allow export of a modified peptide by the Sec-dependent system. Sec-signal sequences are known in the art, see for example Tjalsma et al. 2000 Molecular and Molecular Biology Reviews 64, 515-547. Of particular interest is the signal peptide sequence of the major L. lactis secreted protein Usp45, $SP_{Usp}$. This signal peptide comprises 27 residues and is typical of Gram-positive bacterial signal peptides. The N-terminal region of Usp45 (including $SP_{Usp}$ and, in some cases, several amino acids of the mature protein) has already been used to drive secretion of heterologous proteins in L. lactis, e.g., alpha-amylase, bovine plasmin, IL-2 and IL-6, Nuc, BLG, NSP4 and lipase (see Le Loir Y, et al. Appl Environ Microbiol. 2001; 67(9):4119-27 and references cited therein). As is shown in the Examples below, expression of a nucleic acid construct encoding a polypeptide of the invention comprising a Sec-export signal, a nisin leader peptide and a peptide of interest in a bacterial host cell comprising the Sec-export system and the dehydratase NisB results in the production and secretion of a dehydrated peptide of interest. These data indicate that the lantibiotic leader that is normally present at the N-terminus, is also functional when it is not located at the N-terminus. It has been shown before that short N-terminal extensions of the lantibiotic leader peptide do not interfere with the induction by the lantibiotic leader of lantibiotic enzyme-mediated modifications. A short N-terminal extension with a few amino acids, MDTYRYI (SEQ ID NO:45), of the subtilin leader does not interfere with the capacity of the leader to induce SpaB-mediated dehydration (Stein, T. & Entian, K.-D. 2002. Rapid communications in mass spectrometry. 16, 103-110). Another publication has shown that an N-terminal extension of six histidines (Xie, L. et al. 2004. Science 303, 679-681) still allows LacticinM-driven dehydration and cyclization. It is, however, unexpected that the lantibiotic leader can still function as a signal for the lantibiotic enzymes, i.e. for the dehydratase and the cyclase and the bifunctional LanM enzyme each, despite the fact that it is separated from the N-terminus of the peptide by a much longer N-terminal sequence, which represents an unrelated export signal that allows for the targeting to a non-lantibiotic export system. In short, it is surprising that the lantibiotic leader can function when present internally in the peptide.

Two different Sec-export signal sequences have been placed behind each other (Chen, H. et al. 1996. J. Bacteriol. 178, 6658-6664) in order to investigate preference for one or the other. Two proteins with each a different export signal sequence have also been fused behind each other and in that case the internal signal sequence was functional (Coleman, J. et al. 1985. Cell 43, 351-360). Chimera of signal sequences have been made which each target to a different transport system (Henry, H. et al. 1997. J. Cell Biol. 136, 823-832). Certain naturally occurring proteins contain more than one signal sequence, for instance both an N- and a C-terminal signal sequence (Gerber, L. et al. 1992. J. Biol. Chem. 267, 12168-12173). However, the combination of a lantibiotic leader peptide with a non-lantibiotic export signal sequence has never been described.

In another embodiment of the invention, the Twin-Arginine Translocation (TAT) system is used for export of a peptide that is modified by a lantibiotic-synthesizing enzyme. The TAT system is a bacterial protein export pathway with the remarkable ability to allow the secretion of fully folded proteins and binding of a cofactor does not inhibit translocation (Halbig et al., 1999; Santini et al., 1998). The TAT export system may thus be advantageously used for the export of a thioether-ring containing peptide according to the invention. The TAT system can be present endogenously in the host cell (e.g. Bacillus subtilis) or it can be heterologously expressed in host cells which do normally not contain the TAT system, for example a *Lactococcus lactis* host cell. The export signal sequence required for targeting proteins to the TAT apparatus (also referred to as TAT leader peptides) is longer and less hydrophobic than Sec-specific export signals. (Cristobal et al. 1999). The hydrophobic region in the TAT-specific export signal is significantly shorter due to a higher occurrence of glycine and threonine residues. A hallmark of both plant and prokaryotic TAT-specific export signals is the presence of the consensus motif (S/T-R-R-X-F-L-K (SEQ ID NO:46)) (US2003/0219870 and Berks et al. Mol. Microbiol. 2000; 35(2):260). This sequence motif is located at the amino terminal region/hydrophobic core boundary within export signals of known and suspected TAT substrates. Mutation of one or both of the arginine residues significantly reduces the efficiency of protein translocation. In one embodiment of the invention, a non-lantibiotic export signal bears a characteristic sequence motif for the TAT export system, which includes consecutive arginine residues. Preferably, the export signal contains the consensus sequence mentioned above. However, variants of this consensus motif may also be used, as these have also been reported to be substrates for the TAT pathway (Faury et al. Biochim Biophys Acta. 2004 Jun. 1; 1699(1-2): 155-62). An example of a useful export signal is the TAT leader peptide responsible for the export of YwbN. Other examples are the Tat leader peptide responsible for the export of PhoD (Jongbloed et al. (2004) Molecular Microbiology 54, 1319-1325) and the TAT leader peptides from a gene encoding a protein selected from the group consisting of *E. coli* TorA, Sufi, YacK, YdhX, YdcG, WcaM, YcdB, YaeI, HyaA, HybO, HybA, NapG, NrfC, YagT, YdhX, BisZ, NapA, DmsA, YnfE, YnfF, FdnG, FdoG, YahJ, AmiA, AiC, YcdB, YedY, FhuD and YaeI. The export signal may also be derived from a gene encoding a homologue of any of these sequences. In one embodiment, a polypeptide of the invention comprises not only a TAT export signal but also a protein (or fragment thereof) that is known to be a substrate for the TAT pathway. If said TAT substrate is present upstream of the peptide of interest, it may enhance export of the (modified) peptide of interest by "pulling it along" through the TAT export system. Preferably, the TAT signal sequence and the TAT substrate are derived from the same protein. For example, a polypeptide comprises the YwbN signal sequence and the YwbN protein itself, followed by a leader peptide and a peptide of interest.

In yet another aspect of the invention, a non-lantibiotic ABC (ATP binding cassette)-type export system may be used. For instance, a bacteriocin export system such as the leucocin A and the lactococcin A export system can be used. The export signals for these systems are given in Van Belkum et al. 1997. Mol. Mic. 23, 1293-1301.

Thus, various non-lantibiotic export signals may be used to direct a polypeptide of the invention to a non-lantibiotic export system. Said non-lantibitiotic export signal can be located either at the N- or C-terminus of the polypeptide. However, it is preferred that the export signal is located upstream of the lantibiotic leader sequence to avoid unwanted dehydratation of the export signal or interference with dehydratation of the peptide of interest. Modification of the export signal may interfere with the export of the modified peptide. Thus, preferably the polypeptide comprises from the N- to C-terminus 1) a non-lantibiotic export signal, 2) a lantibiotic leader peptide and 3) a peptide of interest. Surprisingly, it is shown herein that the lantibiotic leader sequence is still functional when it is preceded by a non-lantibiotic export signal. However, polypeptides wherein the export signal is located downstream of the lantibiotic leader peptide are also encompassed by the present invention. For example, provided is a polypeptide comprising the nisin leader sequence, followed by the Sec signal sequence and the peptide of interest.

In one embodiment, the non-lantibiotic export signal is directly followed by the lantibiotic leader peptide (or vice versa if the leader peptide is located upstream of the export signal). It can be envisaged that, if an N-terminal export signal is separated from the lantibiotic leader peptide by a spacer sequence, this will increase the chance of the polypeptide being modified. The leader sequence may in that case be more accessible for recognition by the dehydratase, even if the polypeptide has already encountered the export system. Thus, in another embodiment, the export signal and the leader peptide are separated by a spacer sequence, for example by a spacer sequence of 2-250 amino acid residues in length, for instance 2-50 amino acids or 2-10 amino acids. The spacer can also be larger, such as 200-220 amino acids.

The spacer sequence can comprise any sequence of amino acids, for instance part of the prepropeptide sequence that normally follows the signal sequence. In one embodiment, the spacer sequence is used to provide the polypeptide with a useful peptide sequence. A useful sequence may encode a peptide tag that aids in the detection, isolation or immobilization of the polypeptide after it has been produced and secreted by a host cell. Such tags are known in the art. Examples are the well known His-tag and Myc-tag. In a specific embodiment, the export signal and the leader peptide are separated by a sequence encoding a cell anchor that allows for the display of the modified peptide on the surface of a host cell. Sequences encoding cell anchors are known in the art. For example, WO 02/101026 discloses AcmA-type protein anchor sequences that allow binding of fusion proteins to cell wall material of micro-organisms. Other examples of cell anchors are the repeated sequences of hydrolases (Ghuysen et al. 1994. FEBS Lett 342, 23-28; Margot et al. 1996. Microbiology 142, 3427-3444) or glucosaminidase (Rashid et al. 1995. Microbiology 141, 2391-2404) of *Bacillus subtilis*. An LPxTG tag which allows for covalent coupling to the cell wall (Tjalsma et al. 2000 Microbiology and Molecular Biology Reviews 64, 515-547) can also be used. One or more useful spacer sequence(s) may alternatively be located downstream from the peptide of interest.

It will be clear that the peptide of interest can be any peptide whose modification by a dehydrating and ring forming lantibiotic enzyme is desired. Typically, a peptide of interest is designed such that following post-translational dehydration of one or more serine or threonine residues, the dehydrated residues can be coupled to a cysteine (either by a host cell or in vitro) such that a thioether ring structure is formed. Herewith, it is possible to introduce a stabilizing ring structure at essentially any desired position in the peptide. Of particular interest are peptides with a biological activity, e.g. peptides are intended for therapeutic use, because the introduction of one or more thioether rings generally increases the biostability of the peptide. Furthermore, a ring structure may be used to alter the biological activity, for instance receptor binding affinity or enzyme specificity, of a peptide. The peptide of interest is for example a hormone, an enzyme inhibitor, an enzyme activator, a receptor ligand, an inhibitory peptide, a lantibiotic protein, a viral protein, a eukaryotic protein, a mutant thereof (e.g. specifically designed to allow for a modification at a certain position), a mimic, a homologue or a functional fragment equivalent thereof.

Examples of such peptides are vasopressin, terlipressin, cispressin, allatostatin I, angiotensin I, anthopleurin-A, anti-inflammatory peptide I, dermaseptin, bombin-like peptide, histatin-5, indolicidin, magainin I, atrial natriuretic factor, bradykinin, brain natriuretic peptide, C-type natriuretic peptide, vasonatrin, delta sleep inducing peptide, alpha-dendrotoxin, eledoisin, echistatin, alpha endorphin, beta-endorphin, defensin I, secretin, urocortin, urocortin II, small cardioactive peptide A and B, ceratotoxin A, cerebellin, charybdotoxin, cholecystokinin, conopressin G, alpha-conotoxin E1, corazonin, leu-enkephalin, met-enkephalin, oxytocin, exendin-3, experimental allergic encephalitogenic peptide, experimental autoimmune encephalomyelitis complementary peptide, gonadoliberin II, tocinoic acid, leuprolide, calcitonin, ACTH, corticotropin inhibiting peptide, corticotropin release factor, somatostatin, human pancreatic polypeptide, peptide XY, glucagon, alpha-neurokinin, LHRH1 and 2, brain derived acidic fibroblast growth factor, brain derived basic fibroblast growth factor, insulin, parathormone, fibrinogen binding inhibitor peptide, fibroblast growth factor inhibitory peptide, galanin, gastric inhibitory polypeptide, big gastrin I, pentagastrin, transforming growth factor alpha, human growth hormone, growth hormone release factor, guanylin, helospectin I, intercellular adhesion molecule, tachyplesin I, HIV antigenic peptide gp120, HIV antigenic peptide I fragment (gp 41), HIV antigenic peptide 5, HIV protease inhibitors, insulin-like growth factor-I, IGF II 69-84, interleukin fragment, interleukin II fragment, leukokinin I, leukopyrokinin, mastoparan, melanin-concentrating hormone, melittin, motilin, neuropeptide Y, osteocalcin, (N-acetyl-)beta endorphin, ras oncogene related peptide, albumin, erythropoetin and fragments, alglucerase, gramicidin A, B, C and S, alpha-galactosidase, alteplase, antithrombin III, aprotinin, asparaginase, becaplermin, bone morphogenic protein 7, catalase, cecropin B, cellulase, choriogonadotropin beta, choriogonadotropin alpha, chymopapain, chymotrypsin, big endothelin, *clostridium botulinum* toxin type A and B, collagen, collagenase, dornase alpha, eptacog alpha, etanercept, exendin-4, Faktor VIII, Factor IX, Factor X, Fator XIII, fibronectin, fibrinogen, filgrastim, follitropin alpha, follitropin beta, growth hormone release hormone, pituitary adenylate cyclase activating polypeptide, hyaluronidase, hirudin II, imiglucerase, interleukin 2, interferon alpha-4, interferon-beta, intrinsic factor, invertase, lepirudin, lutropin beta, lysozyme, metalloproteinase inhibitor, neurophysin, papain, pepsin, plasminogen, protamine, prothrombin, protirelin, SC3, sermorelin, streptodornase, streptokinase, thyroglobulin, urokinase, epidermal growth factor, transforming growth factor, leucinostatins, nerve growth factor, gluten exorphins, pardaxin, tyrocidin, mast cell degranulating peptide, tumor necrosis factor, RGD peptides, boinbesin, thymosine, erythropoietin (EPO), thymopoietin, caerulein, dermorphin, tachikinin, cecropin, growth inhibitory factor, vasoactive intestinal cofactor, urotensin I and II, any viral polypeptide or a peptide obtained by using semi randomized primers in which serine/threonine and—if desired—cysteine residues are present.

The peptide can be also be a (mutant of an above mentioned) lantibiotic, a (mutant of a) non-lantibiotic bacteriocin, for instance of bavaricin MN, enterocin P, mesentericin Y105, pediocin PA-1, lactacin F, lactococcin G, plantaricin EF, plantaricin JK, lactococcin A, lactococcin 972, plantaricin A, curvacin A, divercin V41, enterocin A, muntcidin, sakacin P, leukocin A, carnobacteriocin B2, closticin 574, circularin A, microcin J25, gassericin A or AS48. The lantibiotic or bacteriocin may or may not comprise its own leader peptide. Of course, if it comprises its own leader peptide in addition to the lantibiotic leader peptide as defined above, the distance between the leader peptide to be recognized by the dehydratase and the residues to be modified becomes relatively large. For that reason, it may be preferred to remove its own leader peptide such that in the whole polypeptide construct only one lantibiotic leader is present. In certain situations, for instance if the own leader peptide is small, as is for example the case for circularin A, microcin J25, gassericin A and AS48, the presence of an additional leader sequence may not negatively affect modification of the peptide of interest. It can even be envisaged that the presence of distinct leader peptides (e.g. lantibiotic leader peptide as well as bacteriocin leader peptide) is advantageous because this allows for the recognition and modification by distinct modifying enzymes.

As will be clear from the above and the examples below, the invention also provides a method for producing a polypeptide in a host cell, comprising providing a host cell with a recombinant nucleic acid encoding a polypeptide to the invention and allowing expression and secretion of the encoded polypeptide by said host cell. To allow for the desired dehydration of the encoded peptide of interest, said host cell should comprise at least a dehydratase capable of recognizing the encoded leader peptide and dehydrating said encoded polypeptide, and a non-lantibiotic export system capable of secreting said dehydrated polypeptide. The host cell may furthermore comprise a cyclase to allow for intracellular thioether ring formation. The host cell may naturally contain the modifying enzyme(s) (i.e. dehydratase and/or cyclase) or the host cell may be provided with a nucleic acid encoding said enzyme(s). Methods to provide a host cell with a recombinant nucleic acid are known in the art. See for example Sambrook, Fritsch & Maniatis (1989) Molecular Cloning, A laboratory Manual; 2nd Edition, CSHL Press. The genes) encoding the modifying enzyme(s), for instance the NisB gene, may be placed on a single expression plasmid together with the nucleic acid construct encoding a polypeptide of the invention. They may also be placed on two different plasmids, for example on plasmids each having a distinct replicating mechanism. Alternatively, either one or both of the recombinant nucleic acids encoding a modifying enzyme or a polypeptide is introduced in the chromosome of the host cell.

Likewise, the non-lantibiotic export system may be present endogenously in the host cell or it may be provided to the host cell using recombinant DNA technology. Most practically, the non-lantibiotic export system is present endogenously in the host cell.

According to the invention, the host cell can be a prokaryote or a eukaryote, such as a yeast. In one embodiment, a host cell is a Gram-positive prokaryote, such as a *Lactococcus* spp. Lactococci are Gram-positive facultative anaerobes. They are also classified as lactic acid bacteria (LAB). In a specific aspect, a host cell is *Lactococcus lactis* (*L. lactis*), formerly known as *Streptococcus lactis*. For example, *L. lactis* strain NZ9000 can be used. In another embodiment, a *Bacillus* spp. is used as host cell. For example, a *B. subtilis* host cell is used that endogenously contains the Tat export system.

LEGENDS TO THE FIGURES

Figure 1B:
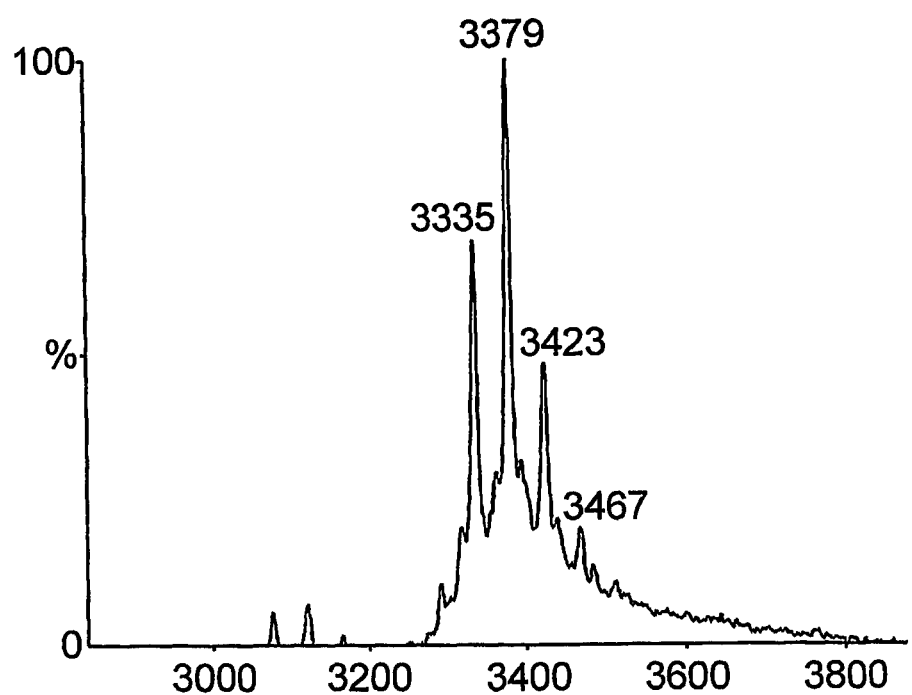
Figure 1C:
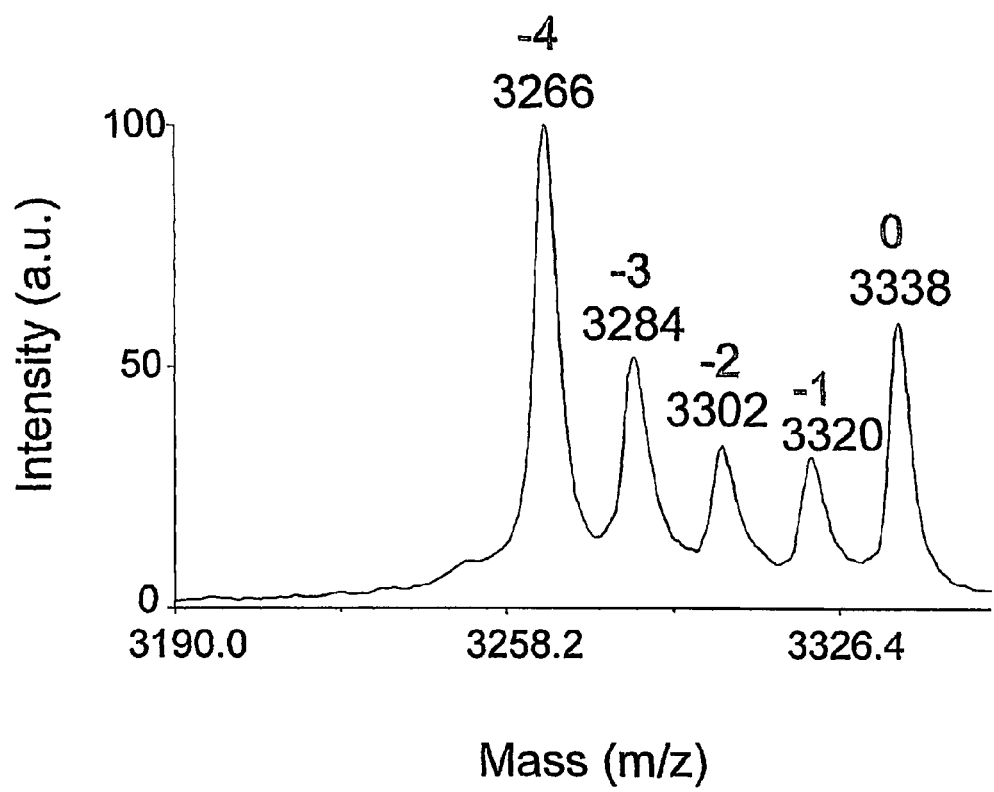

FIG. 1: Export of NisB-dehydrated peptide via the sec system. *Lactococcus lactis* NZ9000 containing pNGnisB and containing pNG411TPPII, which codes for the USP signal sequence followed by the nisin leader followed by a sequence that codes for ITSISRASVA (SEQ ID NO:43) was grown, induced and further cultured overnight. Medium samples were analysed by Maldi TOF MS and show unmodified peptide composed of the nisin leader followed by ITSISRASVA (SEQ ID NO:43) as well as variants with one, two, three and four dehydrations. (FIG. 1A). In order to confirm dehydration of the one threonine and three serines, mass spectrometry analyses (Maldi-TOF MS) of the peptide samples was preceded by treatment with ethanethiol. Ethanethiol treatment results in a mass increase of 63 Da (FIG. 1B). *Lactococcus* lactis NZ9000 containing pILnisB and pNG411TPPII resulted in a strongly enhanced level of dehydration (FIG. 1C).

Figure 2A:
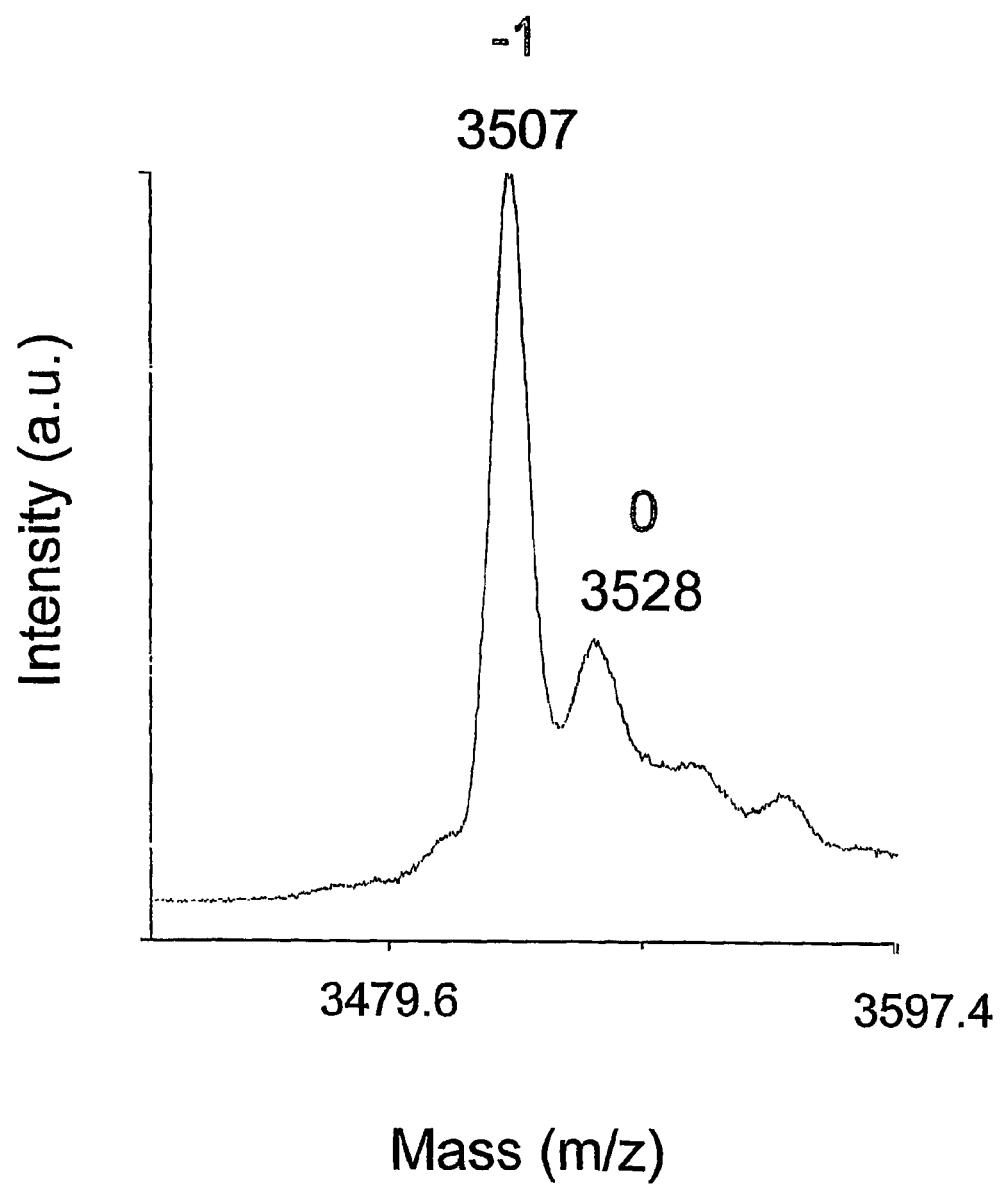
Figure 2B:
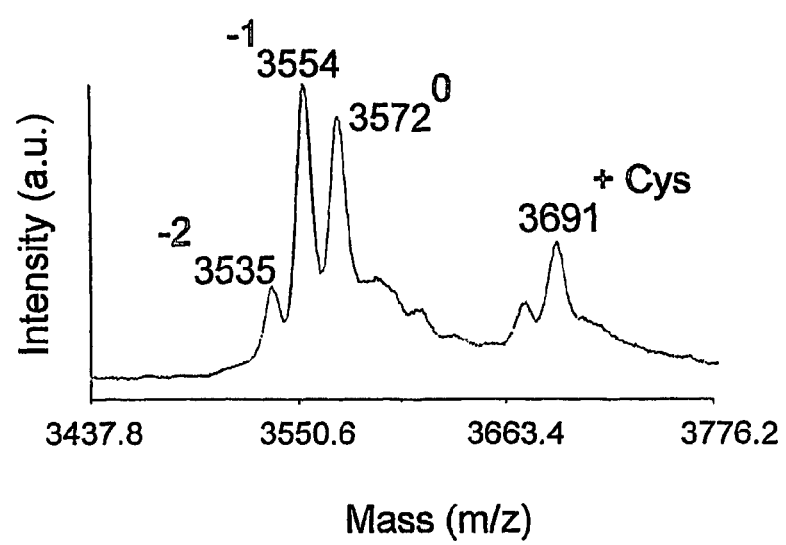

FIG. 2: Export of NisB-dehydrated LHRH variants via the Sec system. Two variants of the Luteinizing Hormone Releasing Hormone peptide (LHRH), LHRH1, QHWSYGCRPG (SEQ ID NO:48), and LHRH2, QHWSYSLRCG (SEQ ID NO:49), were cloned behind the nisin leader sequence which was at the C-terminus of the USP signal sequence. *Lactococcus lactis* NZ9000 containing pILnisB and either pLP-LHRH1 or pLP-LHRH2 was grown to OD 0.4 in minimal medium, induced, cultured overnight and the supernatant was analysed by mass spec. Of LHRH1 a large peak corresponding to leader attached to one time dehydrated LHRH1 (3507 Da) was observed and a small peak corresponding to unmodified LHRH1 (3528 Da) (FIG. 2A). Of LHRH2 peaks of unmodified without (3572 Da) and with cysteine addition (3691 Da) and one time dehydrated (3554 Da) were the most conspicuous. In addition a small peak of two times dehydrated LHRH2 (3535 Da) was observed (FIG. 2B).

Figure 3:
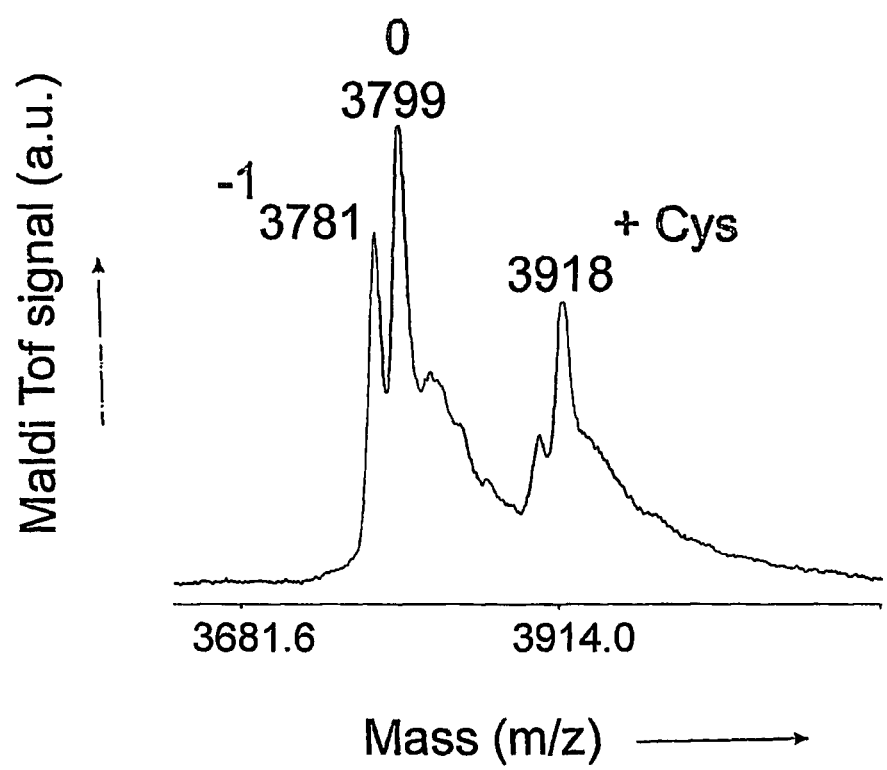

FIG. 3: Export of a NisB-dehydrated erythropoietin variant via the Sec export system. *Lactococcus lactis* NZ9000 containing plasmid pILnisB and containing plasmid pLPepo (encoding the Sec signal sequence preceding the nisin leader preceding the epo fragment YASHFGPLGWVCK (SEQ ID NO:50)) was grown to OD 0.4 in minimal medium, induced and further cultured overnight. Samples were prepared by subjecting host cell culture supernatant to the ZipTip (C18 ZipTip, Millipore) procedure, after which Maldi TOF analysis was applied. Unmodified peptide (3799 Da) and one time dehydrated peptide (3781 Da) is observed.

Figure 4:
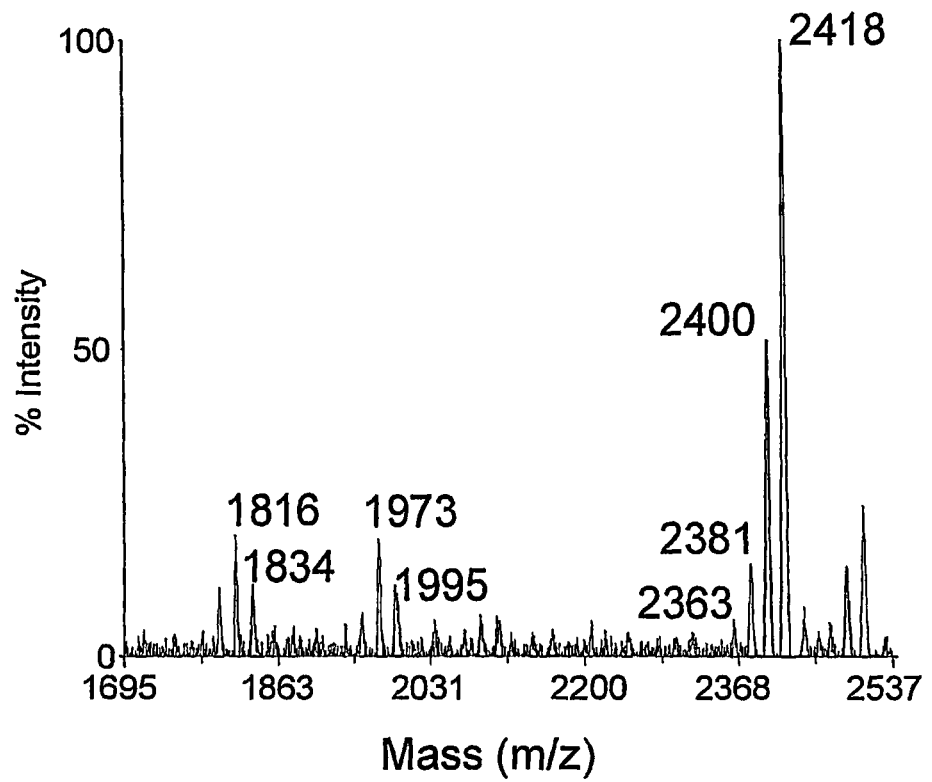

FIG. 4: Export of polypeptide via the Sec export system by using an internal Sec export signal sequence. *L. lactis* NZ9000 containing pILnisB and a second plasmid coding for the nisin leader followed by the sec signal sequence followed by ITSISRASVA (SEQ ID NO:43) was established, grown to OD 0.4 in GM17 medium, spun down and resuspended in minimal medium, induced and further cultured overnight. Samples were prepared by subjecting host cell culture supernatant to the ZipTip (C18 ZipTip, Millipore) procedure, after which Maldi TOF analysis was applied.

FIG. 5: The nisin leader peptide sequence functions internally behind the TAT export signal sequence of YwbN. *L. lactis* cultures were grown on GM17, induced at OD600 equal to 0.4 and grown further overnight. Lysozyme-treated cells were boiled and subjected to gel electrophoresis.

Panel A: overnight overlay of the gel with topagar containing the indicator strain LL108 and trypsin. NZ9000 pIL5BC (1); NZ9000 pIL5BC pNGssPhoDnisA (2); NZ9000 pIL5BC pNGssYwbNnisA (3); commercial nisin (0.5 µg) (4); prenisin (5)

Panel B: overlay with topagar containing LL108 without trypsin. Marker (6); NZ9000 pIL5BC pNGssYwbNnisA (7); nisin (8); prenisin (9).

Figure 6:
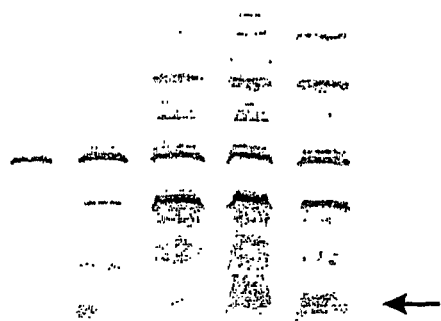

FIG. 6: Export of prenisin out of *Bacillus subtilis* by using the TAT export system secretion signal YwbN at the N-terminus of prenisin. Cells were induced and cultures were grown till stationary phase/late stationary phase. The extent of polypeptide secretion was analyzed by Western blotting using anti-nisin leaderpeptide antibodies. Lane 1: *Bacillus subtilis* containing nisRK on the chromosome. Lanes 2,5: *Bacillus subtilis* containing pNGssYwbNisA; lanes 3,4: *Bacillus subtilis* containing pNGssYwbNnisA and pIL5BC.

The invention will be illustrated by the Examples below.

EXAMPLE 1A

Production and Secretion of a Dehydroalanine-Containing Inhibitor Peptide of Tripeptidylpeptidase II Via the Sec-Export System This example shows the NisB-mediated dehydration and the secretion of a peptide of interest that is N-terminally preceded by the nisin lantibitiotic leader peptide, whose N-terminus is fused to the C-terminus of the Sec-export signal sequence USP. It does not describe the liberation of the inhibitory pentapeptide. Dehydration of the peptide of interest is measured by mass spectrometry analysis on the secreted protein, since each dehydration results in a decrease in mass of 18 Da. The pentapeptide RADhaVA (SEQ ID NO:42) (Dha stands for dehydroalanine i.e. dehydrated serine) is known to inhibit Tripeptidylpeptidase II (TPPII).

Materials:

Plasmid pNGnisB, derived from pNZ8048, with nisB directly, without inverted repeat, behind the nis promoter, encodes the dehydratase of the lantibiotic nisin, NisB. In pNGnisB, the nisB gene is not preceded by an inverted repeat, which is different from the situation on the chromosome of the nisin-producing NZ9700 strain. The nisB gene is directly under control of the nisin promoter. NisB can dehydrate serines and threonines that are present in peptides fused to the C-terminus of the nisin leader. Plasmid pNG411TPPII encodes the USP signal sequence (Van Asseldonk et al. 1990 Gene 95, 155-160; Van Asseldonk et al. 1993 Mol. Gen. Genet. 240, 428-434) followed at the C-terminus by the nisin leader followed by the sequence ITSISRASVA (SEQ ID NO:43). It is under control of the nisin promoter and has four dehydration possibilities, indicated in bold: Sec export signal sequence-nisin leaderpeptide-ITSISRASVA (SEQ ID NO:43). ITSIS (SEQ ID NO:65) are the first five nisin propeptide residues. They precede RASVA (SEQ ID NO:41) in order to enhance export. The total sequence of the polypeptide is: MKKKIISAILMSTVILSAAAPLSGVYAM-STKDFNLDLVSVSKKDSGASPRITSISRASVA (SEQ ID NO:44). It is of note that, for liberating the RADhaVA (SEQ ID NO:42) pentapeptide, a different construct that contains a cleavage site (e.g. a methionine residue) before RASVA (SEQ ID NO:41) is preferred.

The *Lactococcus lactis* NZ9000 host cell contains the genes coding for NisRK, which are involved in nisin-mediated induction of activity of the nisin promoter.

Experiments

*Lactococcus lactis* NZ9000 containing pNGnisB and containing pNG411TPPII was grown to OD 0.4 in minimal medium (Rink et al, 2005), induced and further cultured overnight. Samples were prepared by subjecting host cell culture supernatant to the ZipTip (C18 ZipTip, Millipore) procedure. In order to confirm dehydration, mass spectrometry analyses (Maldi-TOF MS) of the peptide samples was preceded by treatment with ethanethiol. Ethanethiol treatment results in a mass increase of 62 Da.

Results

The results of the analysed supernatant show the unmodified peptide composed of the nisin leader fused to ITSISRASVA (SEQ ID NO:43) and peaks corresponding to this peptide which had undergone four dehydration (−18 Da each, because $H_2O$ has disappeared) steps, evidenced by the appearance of four mass spectrometry peaks (FIG. 1A, Table 3). Ethanethiol modification of the dehydrated peptides confirmed three dehydrations by the appearance of peaks with 45 Da (−18 Da $H_2O$+63 Da ethanethiol) increase per dehydration (FIG. 1B, Table 3).

TABLE 3

Dehydration by NisB and export via the sec system.

|  | no ethanethiol average mass (M + H⁺) (Da) | | ethanethiol average mass (M + H⁺) (Da) | |
| --- | --- | --- | --- | --- |
|  | observed | theoretical | observed | theoretical |
| unmodified | 3339 | 3339 | 3335 | 3339 |
| 1 dehydration | 3321 | 3321 | 3379 | 3384 |
| 2 dehydration | 3303 | 3303 | 3423 | 3429 |
| 3 dehydration | 3286 | 3285 | 3467 | 3474 |
| 4 dehydration | 3267 | 3267 | — | 3519 |

Conclusion

Intracellular NisB, in the absence of all other lantibiotic enzymes, dehydrates the serines and threonine in ITSISRASVA (SEQ ID NO:43) when this peptide is fused to the C-terminus of the nisin leader, which leader is fused to the C-terminus of the USP signal sequence. In addition, this dehydrated peptide is exported after which the USP signal sequence is cleaved off. The USP signal sequence stays bound to the cell membrane. Hence, lantibiotic-enzyme-modified peptides can be exported via non-lantibiotic export systems, in this case the sec system.

EXAMPLE 1B

Improved Dehydration, Production and Secretion of a Dehydroalanine-Containing Inhibitor Peptide of Tripeptidylpeptidase II Via the Sec-Export System This example is nearly identical to example 1A, but instead of plasmid pNGnisB a different plasmid pILnisB was used. pILnisB is derived from vector pIL253 (Simon, D., and Chopin, A. (1988) *Biochimie* 70, 559-566). In pILnisB no inverted repeat is present between the nis promoter and nisB. *Lactococcus lactis* NZ9000 containing pILnisB and containing pNG411TPPII was grown to OD 0.4 in minimal medium, induced and further cultured overnight. Samples were prepared by subjecting host cell culture supernatant to the ZipTip (C18 ZipTip, Millipore) procedure.
Results Peaks (of nisin leader peptide at whose C-terminus the ITSISRASVA (SEQ ID NO:43) sequence) corresponding to unmodified peptide (3338 Da), one time dehydrated (3320 Da), two times dehydrated (3302 Da), three times dehydrated (3284 Da) and a major peak corresponding to four times dehydrated peptide (3266 Da) were observed (FIG. 1C).
Conclusion This example confirms the export of the NisB-dehydrated peptide, composed of the nisin leaderpeptide at which C-terminus the ITSISRASVA (SEQ ID NO:43) peptide, via the sec system directed by the USP signal sequence which is cleaved off. The combination of the pILnisB plasmid, which replicates via a bidirectional mechanism, with the leader construct plasmid derived from pNZ8048, which replicates via a rolling circle mechanism leads to a higher extent of NisB-mediated dehydration.

EXAMPLE 2

Export of Dehydrated Prenisin Via the Sec-Export System

This example demonstrates the intracellular NisB-mediated dehydration of prenisin, which is coupled to the C-terminus of the Sec export signal sequence, followed by Sec-mediated secretion of dehydrated fusion peptide and cleavage of the Sec signal sequence thus liberating dehydrated prenisin extracellularly.
Experiment:

A plasmid (pNG411, derived from pNZ8048) was constructed that codes for the USP signal sequence fused to prenisin. *Lactococcus lactis* NZ9000 containing pNGnisB and pNG411 was induced overnight, cells were spun down and 20 ml of the supernatant was subjected to TCA precipitation. The pellet was resuspended in a small volume and subjected to the ZipTip procedure and Maldi TOF MS. A mass peak corresponding to unmodified prenisin was observed. In addition a mass peak corresponding to fully dehydrated prenisin was observed. Ethanethiol modification of the sample caused complete disappearance of the mass peak that corresponds to fully dehydrated prenisin. This demonstrates that prenisin can be intracellularly modified by NisB in the absence of NisT and NisC and can subsequently be exported due to the N-terminal USP signal sequence. The USP signal sequence is extracellularly cleaved off.

EXAMPLE 3

Export of a NisB-Dehydrated LHRH Variants Via the Sec System

In this example the export of dehydrated Luteinizing hormone release hormone (LHRH) variants via the sec system out of *L. lactis* is demonstrated. LHRH is a decapeptide with the sequence pGluHWSYGLRPG-nh2 (SEQ ID NO:47). Two variants, LHRH1, QHWSYGCRPG (SEQ ID NO:48), and LHRH2, QHWSYSLRCG (SEQ ID NO:49), were cloned behind the nisin leader which was at the C-terminus of the USP signal sequence. The glutamine can, after removal of the leader peptide, i.e. when the glutamine is the most N-terminal residue, spontaneously convert into the pGlu present in LHRH. Both LHRH variants, 1 and 2, can be amidated.
Experiment

*Lactococcus lactic* NZ9000 containing pILnisB and either pLP-LHRH1 or pLP-LHRH2 was grown to OD 0.4 in minimal medium, induced and further cultured overnight. Samples were prepared by subjecting host cell culture supernatant to the ZipTip (C18 ZipTip, Millipore) procedure, after which Maldi TOF analysis was applied.
Results Both LHRH variants with the nisin leader peptide still attached were detected in the culture medium. Of LHRH1 (to which the nisin leader is still attached) a large peak corresponding to one time dehydrated LHRH1 (3507 Da) was observed and a small peak corresponding to unmodified LHRH1 (3528 Da) was measured (FIG. 2A). Of LHRH2 (to which the nisin leader still attached) peaks of unmodified without (3572 Da) and with cysteine addition (3691 Da) and one time dehydrated (3554 Da) were the most conspicuous. In addition a small peak of two times dehydrated LHRH2 (3535 Da) was observed (FIG. 2B).
Conclusion LHRH1 and LHRH2 can be dehydrated by NisB and subsequently exported out of *L. lactis* via the sec system.

EXAMPLE 4

Dehydration and Export of a NisB-Dehydrated Erythropoietin Variant Via the Sec System Erythropoietin (or EPO) is a glycoprotein hormone that is a growth factor for erythrocyte precursors in the bone marrow. It increases the number of red blood cells in the blood. Synthetic erythropoietin is available as an expensive injectable therapeutic agent produced by recombinant DNA technology.

Small mimetic peptides of EPO are known (for an overview see Johnson D L, Jolliffe L K; Nephrol Dial Transplant. 2000 September; 15(9):1274-7). Many of these contain a disulfide bridge responsible for maintaining the peptide in the conformation required for receptor interaction. In the present example one of the disulfide forming cysteines is replaced by serine, thus aiming at dehydration and thioether bridge formation by coupling of the dehydrated serine to the remaining cysteine. A construct containing the USP signal sequence followed by the nisin leader followed by the EPO fragment (underlined) was established on a pNG8048 derived plasmid termed pLPepo. The complete sequence was:

(SEQ ID NO: 51)
MKKKIISAILMSTVILSAAAPLSGVYAMSTKDFNLDLVSVSKKDSGASPR

YASHFGPLGWVCK.

Experiment

*Lactococcus lactis* NZ9000 containing pILnisB and containing pLPepo was grown to OD 0.4 in minimal medium, induced and further cultured overnight. Samples were prepared by subjecting host cell culture supernatant to the ZipTip (C18 ZipTip, Millipore) procedure, after which Maldi TOF analysis was applied.

Results

Maldi TOF analysis revealed peaks corresponding to unmodified leader peptide-epo without (3799 Da) and with cysteine addition (3918 Da) and to one time dehydrated leader peptide-epo (3781 Da) (FIG. 3).

Conclusion

Intracellular NisB, in the absence of all other lantibiotic enzymes, dehydrates the serine in YASHFGPLGWVCK (SEQ ID NO:50) when this peptide is fused to the C-terminus of the nisin leader, which leader is fused to the C-terminus of the USP signal sequence. In addition, this dehydrated peptide is exported after which the USP signal sequence is cleaved off. The USP signal sequence stays bound to the cell membrane. Hence, lantibiotic-enzyme-modified peptides can be exported via non-lantibiotic export systems, in this case the sec system.

EXAMPLE 5

Export of Dehydrated Peptide Via the Sec System

In this example it is demonstrated that a dehydrated peptide can be exported out of *Lactococcus lactis* via the Sec system when the Sec signal sequence is present internally rather than N-terminally.

Experiment

*L. lactis* NZ9000 containing pILnisB and a second plasmid coding for the nisin leader followed by the sec signal sequence followed by ITSISRASVA (SEQ ID NO:43) is established, grown to OD 0.4 in GM17 medium, spun down and resuspended in minimal medium, induced and further cultured overnight. Samples were prepared by subjecting host cell culture supernatant to the ZipTip (C18 ZipTip, Millipore) procedure, after which Maldi TOF analysis was applied. The full length peptide has the following sequence:

(SEQ ID NO: 52)
MSTKDFNLDLVSVSKKDSGASPRMKKKIISAILMSTVILSAAAPLSGVYA

ITSISRASVA.

Results

The following mass peaks are measured (TABLE 4 and FIG. 4):

TABLE 4

| Peptide: ITSISRASVA (SEQ ID NO: 43) preceded by C-terminal sec signal fragment of the following | Observed mass (Da) | Theoretical mass (Da) | —H$_2$O | Ser/Thr present in sec signal fragment |
| --- | --- | --- | --- | --- |
| 15 | 2418 | 2419 | 0 | 3 |
| 15 | 2400 | 2401 | 1 | 3 |
| 15 | 2381 | 2383 | 2 | 3 |
| 15 | 2363 | 2365 | 3 | 3 |
| 11 | 1995 | 1993 | 0 | 2 |
| 11 | 1973 | 1975 | 1 | 2 |
| 11 | 1956 | 1957 | 2 | 2 |
| 11 | 1937 | 1939 | 3 | 2 |
| 9 | 1834 | 1835 | 0 | 1 |
| 9 | 1816 | 1817 | 1 | 1 |
| 9 | 1797 | 1799 | 2 | 1 |
| 6 | 1595 | 1595 | 0 | 1 |
| 6 | 1582 | 1577 | 1 | 1 |
| 6 | 1559 | 1559 | 2 | 1 |
| 6 | 1540 | 1541 | 3 | 1 |

Conclusion

Dehydrated peptides can be exported via the Sec system. Apparently, the fact that intracellularly at the N-terminus the nisin leader is present and that the sec signal sequence is not N-terminally does not eliminate the functionality of the sec signal sequence. Of the peptide composed of nisin leader—sec signal sequence—ITSISRASVA (SEQ ID NO:43), partly dehydrated peptides are exported originating from C-terminal fragments of the Sec signal sequence followed by ITSISRASVA (SEQ ID NO:43). The peptides composed of the 6 C-terminal Sec signal amino acids followed by ITSISRASVA (SEQ ID NO:43) that are 2 and 3 times dehydrated prove that at least two residues of the ITSISRASVA (SEQ ID NO:43) part are dehydrated since the sec signal fragment has only one dehydratable residue.

EXAMPLE 6

The nisin leader functions as a signal for modification by NisB and N is C when present internally in a polypeptide, behind the N-terminal signal sequence of YwbN for the TAT translocation system.

In this example we demonstrate that the nisin leader peptide triggers modification of nisin when prenisin is present behind TAT signal sequences. We use *L. lactis*, a bacterial host cell that does not have a TAT export system. *L. lactis* containing the modification enzymes NisBC and a polypeptide composed of a TAT signal sequence followed by prenisin is induced, disrupted and the homogenate is analysed on gel. After separation on gel an overlay with *L. lactis* 108, sensitive to nisin, is done with and without trypsin. The trypsin cleaves off the leader peptide liberating active nisin. Active nisin becomes visible by halo's that reflect the presence of nisin preventing the growth of the overlaid *L. lactis* 108. The highest position of the halo's on gel, reflects the size of the intact polypeptide and proves that the TAT signal sequence was still attached to fully modified prenisin before trypsin treatment.

Cloning

The signal sequences of PhoD and YwbN were cloned in front of nisA by amplification using chromosomal DNA of *B. subtilis* as template for the primers:

```
ssPhoD.fw
5' TCGGTCTCTCATGGCATACGACAGTCGTTTTG  (SEQ ID NO: 57)
     Bsaii
Tm = 63° C.

ssPhoDrev
5' AAAGTACTAGCATTTACTTCAAAGGCCCCAACC (SEQ ID NO: 58)
     scai
Tm = 66° C.

ssYwbN.fw
5'                                   (SEQ ID NO: 59)
GCGAAGACGCCATGAGCGATGAACAGAAAAAGCC
     Bpii
Tm = 63° C.

ssYwbN.rev
5' AAAGTACTACGCAGTCTGAACAAGCGG       (SEQ ID NO: 60)
Tm = 63° C.
```

The expected fragments of 168 bp (ssPhoD) and 132 bp (ssYwbN) were obtained. Subsequently, ssPhoD was digested with BsaII and ssYwbN with BpI. The obtained fragments were cloned in pNG8048E which was first digested with NcoI and EcoRV. The nisA gene was amplified with the primers:

```
leader.fw1
5' TTAGTACTAAAGATTTTAACTTGGATTTGGTATCTG   (SEQ ID
Tm = 60° C.                                NO: 61)

primer 99
5' GCAATATCAGTAATTGCTTTATCAACTGC          (SEQ ID
Tm = 63° C.                                NO: 62)
```

The obtained fragment of 135 bp was digested with Seal and aflIII and cloned in pNGssPhoD and pNGssYwbN digested with ScaI and XbaI. The obtained plasmids were termed: pNGssPhoDnisA and pNGssYwbNnisA.

Experiment

Figure 5A:
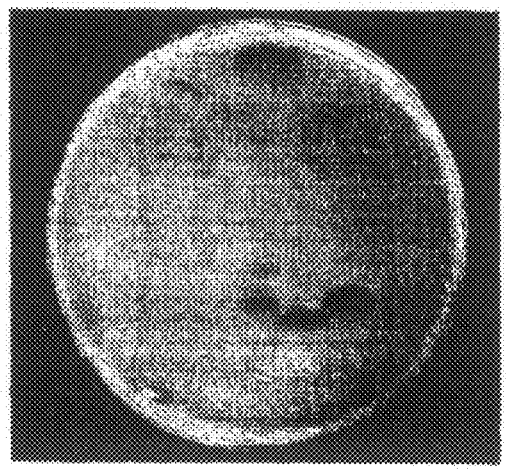
Figure 5B:
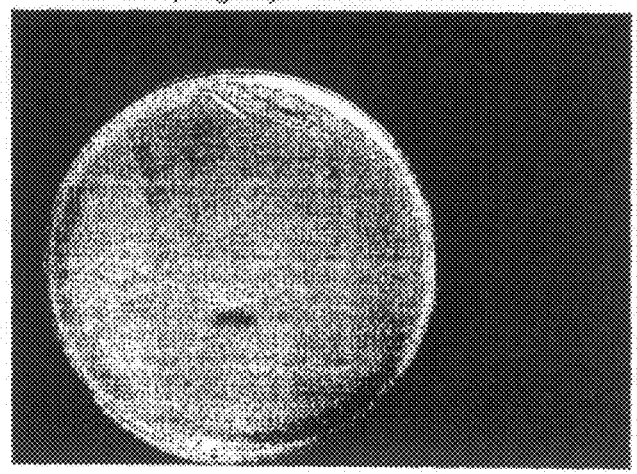

*L. lactis* cultures were grown on GM17 with 5.0 μg/ml erythromycin (selection marker of pILBC) and 5.0 μg/ml chloramphenicol (selection marker of pNGssPhoDnisA or pNGssYwbNnisA). At OD600 equals 0.4 cultures were induced with nisin (1/1000 sup of *L. lactis* strain NZ9700) and grown further. Cells were harvested in the late stationary phase. 1 ml cells was spun down, dissolved in 50 μl 50 mM Tris pH6.8 containing lysozyme, and incubated for 20 min at 55° C. 50 μl 2×SB was added and samples were boiled for 5 min at 100° C. 20 μl was put on a tricine gel. After electrophoreses the gel was thoroughly washed with water to remove the SDS. The gel was divided in two. One part was overlaid with top-agar containing the indicator strain L1108 (*Lactococcus lactis* pORI280, erythromycin and chloramphenicol sensitive) (Methods in Cell Science 20, 35-50) and 0.01 mg/ml trypsin (FIG. 5A). The other part was overlaid with top-agar and L1108 but without trypsin (FIG. 5B). Plates were incubated overnight.

Conclusions

Very clearly, NisBC are capable of modifying prenisin when it is present behind the YwbN signal sequence. Trypsin cleaves off the nisin leader and at the same time the YwbN signal sequence attached to the nisin leader. The site of the highest halo proves that during the modification by NisBC the YwbN signal sequence was attached to the prenisin (FIG. 5A). Prenisin and nisin itself run further on the gel and give halo's at lower sites. Negative controls give no halo, hence no other proteins or peptides cause halo formation. Full length peptide with PhoD signal sequence gives a faint halo (FIG. 5A). Except for the lane with nisin itself, no halo's are observed in the absence of trypsin (FIG. 5B).

EXAMPLE 7A

Use of the TAT Signal Sequence of YwbN for Export of Nisin Out of *Bacillus subtilis*

In this example the TAT signal sequence of YwbN is cloned N-terminally from prenisin. The sequence encoding the polypeptide is expressed in *B. subtilis* as host cell and export out of *B. subtilis* is measured. *Bacillus* contains the TAT export system endogenously.

Cloning and Methods

First, nisRK was inserted in a *Bacillus subtilis* 168 strain (AEM 70, 5704-7). The integration vector pTPnisRK was constructed by amplification with DNA Phusion polymerase of nisRK on the chromosome using the primers:

```
AAAGAATTCCCTGTTACTGGAGATGGAGAAG      (SEQ ID NO: 63)
   EcoRI
P-NisR.fw1 Tm = 61° C.

AAACCCGGGCAATTTTCAGAATCTATTCAGAAAC   (SEQ ID NO: 64)
   XmaI
NisK.rev1 Tm = 56° C.
```

The amplified fragment digested with XmaI was cloned in pBM1 digested with SnabI and XmaI. This resulted in the plasmid pTPnisRK, which does not replicate in *Bacillus*. Integration in the AmyE locus *Bacillus* is performed. The *Bacillus* transformants are resistant to erythromycin and blue coloured when grown on X-gal. Excision was allowed by growing culture for 48 hours without erythromycin. Those cells whose plasmid sequence containing lacZ was excised and which had NisRK still present on the AmyE locus, were white when grown on LacZ, Em-sensitive and amylase negative. Subsequently *Bacillus subtilis* with nisRK on the chromosome, BsnisRK, containing pNGssYwbNisA and BsnisRK containing pNGssYwbNnisA and pIL5BC were established. pNGssYwbNnisA codes for the signal sequence of YwbN followed by prenisin. pIL5BC codes for NisBC.

Experiment.

Secretion was analyzed by Western blotting using antinisin leader peptide antibodies (J. Biol. Chem. 279, 22176-22182) Cultures were grown until stationary phase/late stationary phase and 6 to 8 ml culture was spun down. Supernatant was collected and TCA was added to a final concentration of 10% TCA. Samples were precipitated on ice for 2 hours or o/n at 4° C. Pellets were dissolved in 100 μl MQ. From this solution 15 μl was taken and 15 μl 2×SB was added. 20 μl was put on a tricine gel.

Results and Conclusion.

For both BsnisRK, containing pNGssYwbNisA (lanes 2, 5 of FIG. 6) and BsnisRK containing pNGssYwbNnisA and pIL5BC (lanes 3, 4 of FIG. 6) extracellularly peptide of the expected size could be demonstrated by Western blotting, which was absent in the supernatant of BsnisRK without plasmid. This proves that the non-lantibiotic TAT signal sequence of YwbN directs export of prenisin out of *Bacillus subtilis* in the absence and in the presence of the thioether ring forming enzymes NisBC.

EXAMPLE 7B

Export of Modified Peptide Via the TAT Export System in *Bacillus subtilis*

This example describes the modification and export of prenisin out of *Bacillus subtilis*. To further enhance the efficiency of secretion of the modified polypeptide by the TAT system, an additional sequence is introduced in the polypeptide described in Example 7A. In between the YwbN signal sequence and the nisin-leader peptide sequence, a sequence encoding for the YwbN protein itself is inserted. It is believed that the combined presence of the YwbN signal sequence as well as the YwbN "helper sequence" enhances the export of the peptide located C-terminally from them.

Insert nisRK and nisBC in the chromosome of *Bacillus subtilis*. Transform this strain with a plasmid termed pNGYwbN-nis, coding for a polypeptide comprising, from N- to C-terminus, the YwbN signal sequence (non-lantibiotic export signal), YwbN (helper sequence), nisin-leader (lantibiotic leader peptide) and nisin (peptide of interest). Grow the established *B. subtilis* host cells containing nisRKBC and pNGYwbN-nis overnight on plates. Overlay the cells with induced (1/1000 of supernatant of *Lactococcus lactis* NZ9700) *L. lactis* containing pNGnisP. After subsequent overnight incubation halo's are formed reflecting the liberation of exported nisin, which is cleaved from the YwbN and nisin leader by N is P. Obtain further proof by growing *B. subtilis* containing nisRKBC and pNGYwbN-nis overnight, treat the medium with *L. lactis* containing pNGnisP. Analyse the culture medium by mass spectrometry to identify a peak corresponding to fully modified nisin.

TABLE 1A

```
                          (1) 1         10        20        30       42
     ButyrivibriocinOR79A (1) ----------MNKELNASTNPIDEK---ELEQIIGG------ (SEQ ID NO: 22)
          RuminococcinA   (1) ----------MRNDVLTSTNPMEEK---ELEQIIGG------ (SEQ ID NO: 21)
          Salivaricin-A   (1) -------MNAMKNSKDISNNATEEVSSKELMEVAGG------ (SEQ ID NO: 18)
            Salivaricin   (1) ----------MKNSKDISTNATEEVSSKELMEVAGG------ (SEQ ID NO: 25)
               Variacin   (1) ---------------MTNAFQSLDEVIDAELDAISGG------ (SEQ ID NO: 15)
              Mutacin11   (1) ----------MNKLNSNAVVSSNEVSDSELDTILGG------ (SEQ ID NO: 16)
             Bacteriocin  (1) -----------MKEQNSFNLSQEVTESELDLILGA------ (SEQ ID NO: 24)
             Lacticin-481 (1) -----------MKEQNSFNLSQEVTESELDLILGA------ (SEQ ID NO: 24)
       StreptococcinAFF22 (1) ----------MEKNNEVINSIQEVSLEELDQIIGA------ (SEQ ID NO: 17)
       StreptococcinAM49  (1) ----------MTKEHEIINSIQEVSLEELDQIIGA------ (SEQ ID NO: 23)
             CytolysisLL  (1) -----------MENLSVVPSFEELSVEEMEAIQGSGDVQAE (SEQ ID NO: 34)
             CytolysinLS  (1) MLNKENQENYYSNKLELVGPSFEELSLEEMEAIQGSGDVQAE (SEQ ID NO: 35)
               Sublancin  (1) ----------------MEKLFKEVKLEELENQKGS------ (SEQ ID NO: 19)
              BovicinHJ50 (1) ----------MMNATENQIFVETVSDQELEMIGG------ (SEQ ID NO: 27)
            Lacticin1347A1 (1) --------MNKNEIETQPVTWSEEVSDQNFDEDVFGA----- (SEQ ID NO: 29)
          StaphylococcinC55? (1) -----MKSSFLEKDIEEQVTWFEEVSSQEFDDDIFGA----- (SEQ ID NO: 30)
               Consensus  (1)                L NSLEEVSE ELD ILGG         (SEQ ID NO: 50)
```

```
                      (1) 1       10        20        30        40        50
       Cinnamycin     (1) --------------MTASILQQSVVDADFRAASLENPAAFGASAAALPTPVEAQDQASLDFQTKDIAA
                          (SEQ ID NO: 36)
       Plantaricinw?  (1) --------------MKISKIEAQARKDFFKKIDTNSNLLNVNGA-----------------------
                          (SEQ ID NO: 28)
       Epicidin-280   (1) -------------------MENKKDSFDLEIKKDNME-NNNELEAQ--------------------
                          (SEQ ID NO: 2)
       Pep-5          (1) -------------------MKNNKNSFDLEIKKETSQ-NYDELEPQ--------------------
                          (SEQ ID NO: 3)
       Epilancin-K7   (1) ---------------------MNNSSFDLNINKGVET-QKSDLSPQ--------------------
                          (SEQ ID NO: 4)
Epidermin/[Val1-Leu6]- (1) -----------------MEAVKEKNDSFNLDVKVNAKESNDSGAEPR-------------------
       epidermin           (SEQ ID NO: 9)
       Gallidermin    (1) -----------------MEAVKEKNESFDLDVKVNAKESNDSGAEPR-------------------
                          (SEQ ID NO: 11)
       Nisin-A/Z      (1) ---------------------MSTKDFNLDLVSVSKK--DSGASPR--------------------
                          (SEQ ID NO: 5)
       Nisin          (1) ---------------------MSTKDFNLDLVSVSKK--DSGASPR--------------------
                          (SEQ ID NO: 6)
```

-continued

| | | |
|---|---|---|
| Subtillin/Ericin | (1) | ----------------------MSKFDDFDLDVVKVSKQ--DSKITPQ-------------------- |
| | | (SEQ ID NO: 7) |
| Streptin | (1) | --------------------MNNTIKDFDLDIKTNKKD--T--ATPY-------------------- |
| | | (SEQ ID NO: 26) |
| Sap-B | (1) | ------------------------MNLFDLQSMETPKEEAMGDVE---------------------- |
| | | (SEQ ID NO: 1) |
| LactocinS | (1) | -------------------MKTEKKVLDELSLHASAKMGARDVESSMNAD----------------- |
| | | (SEQ ID NO: 20) |
| Mutacin-1140/III/I | (1) | -------MSNTQLLEVLGTETFDVQEDLFAFDTTDTTIVASNDDPDTR-------------------- |
| | | (SEQ ID NO: 12) |
| Lacticin3147A2 | (1) | ----------------MKEKNMKKNDTIELQLGKYLEDDMIELAEGDESHGG--------------- |
| | | (SEQ ID NO: 32) |
| StaphylococcinC55beta | (1) | ----------------MKNELGKFLEENELELGKFSESDMLEITDDEVYAA---------------- |
| | | (SEQ ID NO: 33) |
| Mersacidin | (1) | MSQEAIIRSWKDPFSRENSTQNPAGNPFSELKEAQMDKLVGAGDNEAA-------------------- |
| | | (SEQ ID NO: 37) |
| Plantaricinwbeta | (1) | ------------MTKTSRRKNAIANYLEPVDEKSINESFGAGDPEAR-------------------- |
| | | (SEQ ID NO: 31) |
| Consensus | (1) | LFDLDL                          E |
| | | (SEQ ID NO: 56) |

Tables 1A and 1B: Alignments of lantibiotic leader peptides. Possible consensus sequences derivable from the alignments are also indicated.

TABLE 2

| | | |
|---|---|---|
| Sap-B | MNLFDLQSMETPKEEAMGDVE | (SEQ ID NO: 1) |
| Epicidin-280 | MENKKDLFDLEIKKDNMENNNELEAQ | (SEQ ID NO: 2) |
| Pep-5 | MKNNKNLFDLEIKKETSQNTDELEPQ | (SEQ ID NO: 3) |
| Epilancin-K7 | MNNSLFDLNLNKGVETQKSDLSPQ | (SEQ ID NO: 4) |
| Nisin-A/Z | MSTKDFNLDLVSVSKKDSGASPR | (SEQ ID NO: 5) |
| Nisin Q | MSTKDFNLDLVSVSKTDSGASTR | (SEQ ID NO: 6) |
| Subtilin/Ericin S/-A | MSKFDDFDLDVVKVSKQDSKITPQ | (SEQ ID NO: 7) |
| Epidermin/[Val1-Leu6]-epidermin | MEAVKEKNDLFNLDVKVNAKESNDSGAEPR | (SEQ ID NO: 9) |
| Gallidermin | MEAVKEKNELFDLDVKVNAKESNDSGAEPR | (SEQ ID NO: 10) |
| Mutacin-1140IIII/I | MSNTQLLEVLGTETFDVQEDLFAFDTTDTTIVASNDDPDTR | (SEQ ID NO: 12) |
| Lacticin-481 | MKEQNSFNLLQEVTESELDLILGA | (SEQ ID NO: 13) |
| Truncated Lacticin-481 | LQEVTESELDLILGA | (SEQ ID NO: 14) |
| Variacin | MTNAFQALDEVTDAELDAILGG | (SEQ ID NO: 15) |
| Mutacin-II | MNKLNSNAVVSLNEVSDSELDTILGG | (SEQ ID NO: 16) |
| Streptococcin-A-FF22 | MEKNNEVINSIQEVSLEELDQIIGA | (SEQ ID NO: 17) |
| Salivaricin-A | MNAMKNSKDILNNAIEEVSEKELMEVAGG | (SEQ ID NO: 18) |
| Sublancin | MEKLFKEVKLEELENQKGS | (SEQ ID NO: 19) |
| Lactocin-S | MKTEKKVLDELSLHASAKMGARDVESSMNAD | (SEQ ID NO: 20) |
| Ruminococcin A | MRNDVLTLTNPMEEKELEQILGG | (SEQ ID NO: 21) |
| Butyrivibriocin OR79A | MNKELNALTNPIDEKELEQILGG | (SEQ ID NO: 22) |
| Streptococcin A-M49 | MTKEHEIINSIQEVSLEELDQIIGA | (SEQ ID NO: 23) |
| Bacteriocin J46 | MKEQNSFNLLQEVTESELDLILGA | (SEQ ID NO: 24) |

TABLE 2-continued

| | | |
|---|---|---|
| Salivaricin A1 | MKNSKDILTNATEEVSEKELMEVAGG | (SEQ ID NO: 25) |
| Streptin | MNNTIKDFDLDLKTNKKDTATPY | (SEQ ID NO: 26) |
| Bovicin HJ50 | MMNATENQIFVETVSDQELEMLIGG | (SEQ ID NO: 27) |
| Plantaricin-Wα | MKISKIEAQARKDFFKKIDTNSNLLNVNGA | (SEQ ID NO: 28) |
| Lacticin-3147A1 | MNKNEIETQPVTWLEEVSDQNFDEDVFGA | (SEQ ID NO: 29) |
| Staphylococcin-C55☐ | MKSSFLEKDIEEQVTWFEEVSEQEFDDDIFGA | (SEQ ID NO: 30) |
| Plantaricin-WB | MTKTSRRKNAIANYLEPVDEKSINESF GAGDPEAR | (SEQ ID NO: 31) |
| Lacticin-3147A2 | MKEKNMKKNDTIELQLGKYLEDDMIEL AEGDESHGG | (SEQ ID NO: 32) |
| Staphylococcin-055☐ | MKNELGKFLEENELELGKFSESDMLEI TDDEVYAA | (SEQ ID NO: 33) |
| Cytolysin-LL | MENSLSVVPSFEELSVEEMEAIQGSGDVQAE | (SEQ ID NO: 34) |
| Cytolysin-LS | MLNKENQENYYSNKLELVGPSFEELSL EEMEAIQGSGDVQAE | (SEQ ID NO: 35) |
| Cinnamycin | MTASILQQSVVDADFRAALLENPAAFGASA AALPTPVEAQDQASLDFWTKDIAATEAFA | (SEQ ID NO: 36) |
| Mersacidin | MSQEAIIRSWKDPFSRENSTQNPAGNP FSELKEAQMDKLVGAGDNEA | (SEQ ID NO: 37) |

The invention claimed is:

1. A nucleic acid encoding a synthetic polypeptide, the polypeptide comprising:
   a first, non-lantibiotic export signal peptide that is SEQ ID NO:46 or a signal for the secretory (Sec) system from *Lactococcus lactis*;
   a second, lantibiotic leader peptide that is recognized by a lantibiotic dehydratase selected from the group consisting of lantibiotic dehydratase (LanB) and lantibiotic bifunctional enzyme (LanM) dehydratase; and
   a third peptide of interest comprising at least one serine or threonine residue that can be posttranslationally dehydrated by LanB, wherein the peptide of interest is positioned C-terminally of both the non-lantibiotic export signal peptide and the lantibiotic leader peptide.

2. The nucleic acid of claim 1, wherein the peptide of interest further comprises at least one cysteine residue that can be coupled enzymatically or chemically to a dehydrated serine or threonine residue.

3. The nucleic acid of claim 2, wherein the cysteine residue is located no more than 30 amino acid residues from the serine or threonine residue in the peptide of interest.

4. The nucleic acid of claim 1, wherein the lantibiotic leader peptide is SEQ ID NO:53 or SEQ ID NO:54.

5. The nucleic acid of claim 1, wherein the lantibiotic leader peptide is from a lantibiotic selected from the group consisting of nisin A, nisin Z, subtilin, ericin S, ericin A, streptin, epidermin, val1-leu6-epidermin, gallidermin, mutacin 1140, mutacin B-Ny266, mutacin III, mutacin I, pep5, epilancin K7, epicidin 280, lacticin 481, variacin, mutacin II, streptococcin A-FF22, salivaricin A, lactocin S, cypemycin, plantaricin C, actagardine, Ala(0)-actagardine, lacticin 3147A1, lacticin 3147A2, staphylococcin C55α, staphylococcin C55b, plantaricin Wa, plantaricin Wb, cytolysin Ll, cytolysin Ls, ruminococcin A, carnocin U149, macedocin, bovicin HJ50, nukacin ISK 1 butyrivibriocin OR79A, cinnamycin, duramycin, ancovenin, mersacidin, and sapB.

6. The nucleic acid of claim 1, wherein the non-lantibiotic export signal peptide is located N-terminally from the lantibiotic leader peptide.

7. The nucleic acid of claim 1, wherein the non-lantibiotic export signal and the lantibiotic leader peptide are separated by between 2 and 250 amino acids.

8. The nucleic acid of claim 1, wherein the peptide of interest is selected from the group consisting of a bioactive peptide, a hormone, an enzyme, an inhibitory protein, a therapeutic protein, a lantibiotic protein, a viral protein and a mutant of any thereof.

9. The nucleic acid of claim 1, wherein the non-lantibiotic export signal peptide is located C-terminally from the lantibiotic leader peptide.

10. The nucleic acid of claim 1, wherein the non-lantibiotic export signal peptide is SEQ ID NO:46.

11. A host cell transformed with the nucleic acid of claim 1.

12. The host cell of claim 11, wherein the host cell is selected from the group consisting of a prokaryote, a eukaryote, a Gram-positive prokaryote, a *Lactococcus* spp. and a *Bacillus* spp.

13. A method for secreting a synthetic polypeptide from a host cell, the method comprising:
   providing the host cell of claim 11;
   expressing the nucleic acid encoding the synthetic polypeptide in the host cell, to produce the synthetic polypeptide in the host cell; and
   secreting the synthetic polypeptide from the host cell, wherein the host cell comprises the lantibiotic dehydratase and the non-lantibiotic export system.

14. The method according to claim 13, wherein the host cell further comprises a lantibiotic cyclase so as to allow production of a thioether-ring in the peptide of interest in the host cell.

15. A nucleic acid encoding a synthetic polypeptide, the polypeptide comprising:
a first peptide consisting of SEQ ID NO:46;
a second, lantibiotic leader peptide; and
a third peptide of interest comprising at least one serine or threonine residue that can be posttranslationally dehydrated by dehydratase, wherein the peptide of interest is positioned C-terminally of both SEQ ID NO:46 and the lantibiotic leader peptide.

16. The nucleic acid of claim 15, wherein the lantibiotic leader peptide consists of the sequence of SEQ ID NO:53 or the sequence of SEQ ID NO:54.

17. A nucleic acid molecule encoding a synthetic polypeptide, the nucleic acid molecule comprising:
a first nucleotide sequence encoding a peptide selected from the group consisting of:
an export signal peptide of a secretory (Sec) system,
an export signal peptide of a Twin-Arginine Translocation (TAT) system, and
an export signal peptide of a non-lantibiotic ATP Binding Cassette (ABC) export system;
a second nucleotide sequence encoding a peptide selected from the group consisting of SEQ ID NO:53 and SEQ ID NO:54; and
a third nucleotide sequence encoding a peptide of interest comprising a serine or threonine residue that can be posttranslationally dehydrated by dehydratase, wherein the third nucleotide sequence is positioned 3' of both the first and second nucleotide sequence in the nucleic acid construct.

18. The nucleic acid molecule of claim 17, wherein the first nucleotide sequence encodes the polypeptide of SEQ ID NO:46.

19. A nucleic acid encoding a polypeptide that is synthetic, the polypeptide comprising:
a first, export signal peptide that is SEQ ID NO:46 or an export signal peptide for the secretory (Sec) system from *Lactococcus lactis*;
a second, leader peptide selected from the group consisting of SEQ ID NO:53 and SEQ ID NO:54; and
a third, peptide of interest comprising at least one serine or threonine residue that can be posttranslationally dehydrated by dehydratase, wherein the peptide of interest is positioned C-terminally of both the export signal peptide and the leader peptide.

20. The nucleic acid of claim 19, wherein the serine or threonine residue can be post-translationally dehydrated by lantibiotic dehydratase (LanB) or lantibiotic bifunctional enzyme (LanM) dehydratase, and wherein the peptide of interest further comprises at least one cysteine residue that can be coupled enzymatically or chemically to a dehydrated serine or threonine residue.

21. The nucleic acid of claim 19, wherein the second peptide is from a lantibiotic selected from the group consisting of nisin A, nisin Z, subtilin, ericin S, ericin A, streptin, epidermin, val1-leu6-epidermin, gallidermin, mutacin 1140, mutacin B-Ny266, mutacin III, mutacin I, pep5, epilancin K7, epicidin 280, lacticin 481, variacin, mutacin II, streptococcin A-FF22, salivaricin A, lactocin S, cypemycin, plantaricin C, actagardine, Ala(0)-actagardine, lacticin 3147A1, lacticin 3147A2, staphylococcin C55α, staphylococcin C55b, plantaricin Wa, plantaricin Wb, cytolysin Ll, cytolysin Ls, ruminococcin A, carnocin U149, macedocin, bovicin HJ50, nukacin ISK-1, butyrivibriocin OR79A, cinnamycin, duramycin, ancovenin, mersacidin, and sapB.

22. The nucleic acid of claim 19, wherein the first and the second peptides are separated by between 2 and 250 amino acids.

* * * * *